US012788739B2

(12) United States Patent
Pasco et al.

(10) Patent No.: US 12,788,739 B2
(45) Date of Patent: Nov. 10, 2026

(54) ANTICANCER FORMULATION

(71) Applicant: University of Mississippi, University, MS (US)

(72) Inventors: David Pasco, University, MS (US); Shivendra Singh, University, MS (US); Premalatha Balachandran, University, MS (US); Mohamed Ali Ibrahim, University, MS (US); Pier Paolo Claudio, University, MS (US); Linda Eastham, University, MS (US); Flavia De Carlo, University, MS (US)

(73) Assignee: University of Mississippi, University, MS (US)

( * ) Notice: Subject to any disclaimer, the term of this patent is extended or adjusted under 35 U.S.C. 154(b) by 906 days.

(21) Appl. No.: 17/275,893

(22) PCT Filed: Sep. 16, 2019

(86) PCT No.: PCT/US2019/051354

§ 371 (c)(1),
(2) Date: Mar. 12, 2021

(87) PCT Pub. No.: WO2020/056425

PCT Pub. Date: Mar. 19, 2020

(65) Prior Publication Data

US 2022/0079912 A1 Mar. 17, 2022

Related U.S. Application Data

(60) Provisional application No. 62/731,586, filed on Sep. 14, 2018.

(51) Int. Cl.

*A61K 31/343* (2006.01)
*A61K 31/155* (2006.01)

(Continued)

(52) U.S. Cl.

CPC .......... *A61K 31/343* (2013.01); *A61K 31/155* (2013.01); *A61K 31/4412* (2013.01); *A61K 31/566* (2013.01); *A61K 45/06* (2013.01)

(58) Field of Classification Search

CPC .. A61K 31/343; A61K 31/155; A61K 31/352; A61K 31/4412; A61K 31/566;

(Continued)

(56) References Cited

U.S. PATENT DOCUMENTS

2017/0189425 A1 7/2017 Bannister et al.

FOREIGN PATENT DOCUMENTS

WO WO-2016049012 A1 * 3/2016 ............. A61P 35/00
WO 2016118842 A1 7/2016

OTHER PUBLICATIONS

Zhu et al., Metformin potentiates anti-tumor effect of resveratrol on pancreatic cancer by down-regulation of VEGF-B signaling pathway, Oncotarget, 7, pp. 84190â84200 (Year: 2016).*

(Continued)

*Primary Examiner* — Jeffrey S Lundgren
*Assistant Examiner* — Alexander K. Showalter
(74) *Attorney, Agent, or Firm* — Thomas | Horstemeyer, LLP

(57) ABSTRACT

Compositions of a glycolysis inhibitor and a mitochondrial complex I inhibitor or glucose-6-phosphate dehydrogenase inhibitor are described. Methods of treating metabolic disorders by administration of a composition comprising glycolysis inhibitor and a mitochondrial complex I inhibitor or glucose-6-phosphate dehydrogenase inhibitor are also described. Also described are methods of inhibiting the proliferation of cancer cells by administration of a therapeutically effective amount of a composition comprising a glycolysis inhibitor and a mitochondrial complex I inhibitor or glucose-6-phosphate dehydrogenase inhibitor.

16 Claims, 24 Drawing Sheets

(51) Int. Cl.

| | |
|---|---|
| ***A61K 31/34*** | (2006.01) |
| ***A61K 31/365*** | (2006.01) |
| ***A61K 31/4412*** | (2006.01) |
| ***A61K 31/566*** | (2006.01) |
| ***A61K 31/5685*** | (2006.01) |
| ***A61K 36/65*** | (2006.01) |
| ***A61K 45/06*** | (2006.01) |
| ***A61P 3/10*** | (2006.01) |
| ***A61P 35/00*** | (2006.01) |

(58) Field of Classification Search
CPC ...... A61K 45/06; A61K 31/34; A61K 31/365; A61K 31/5685; A61K 36/65; A61K 2300/00; A61P 3/10; A61P 35/00
See application file for complete search history.

(56) References Cited

OTHER PUBLICATIONS

Singh et al., The Oligostilbene Gnetin H Is a Novel Glycolysis Inhibitor That Regulates Thioredoxin Interacting Protein Expression and Synergizes with OXPHOS Inhibitor in Cancer Cells, Int. J. Mol. Sci., 24, article 7741, pp. 1-24 (Year: 2023).*
Wilson et al., Molecular Targeting of RRM2, NF-ÃÂ°B, and Mutant TP53 for the Treatment of Triple-Negative Breast Cancer, Mol. Canc. Ther., 20, pp. 655-664 (Year: 2021).*
Deer et al., Phenotype and Genotype of Pancreatic Cancer Cell Lines, Pancreas, 39, pp. 425-435 (Year: 2010).*
Duta-Bratu et al., Resveratrol and Other Natural Oligomeric Stilbenoid Compounds and Their Therapeutic Applications, Plants (Basel), 12, article No. 2935, pp. 1-16 (Year: 2023).*
Gao et al., The resveratrol oligomers, cis- and trans-gnetin H, from Paeonia suffruticosa seeds inhibit the growth of several human cancer cell lines, J. Ethnopharmacol., 169, pp. 24-33 (Year: 2015).*
Kim et al., Cytotoxic and antimutagenic stilbenes from seeds of Paeonia lactiflora, Arch. Pharmacal. Res., 25, pp. 293-299 (Year: 2002).*
Sandoval-AcuÃ±a et al., Inhibition of mitochondrial complex I by various non-steroidal anti-inflammatory drugs and its protection by quercetin via a coenzyme Q-like action, Chem. Biol. Interact., 199, pp. 18-28 (Year: 2012).*
Ai et al., Aspirin inhibits glucoseâ6âphosphate dehydrogenase activity in HCT 116 cells through acetylation: Identification of aspirin-acetylated sites, Mol. Med. Rep., 14, pp. 1726-1732 (Year: 2016).*
Pustovalova et al., The p53-53BP1-Related Survival of A549 and H1299 Human Lung Cancer Cells after Multifractionated Radiotherapy Demonstrated Different Response to Additional Acute X-ray Exposure, Int. J. Mol. Sci., 21, art. 3342 pp. 1-21 (Year: 2020).*
Wang et al., Therapeutic Targeting of TP53-mutated Acute Myeloid Leukemia by Inhibiting HIF-1Î± with Echinomycin, Oncogene, 39, pp. 3015â3027 (Year: 2020).*
Zhu et al., Metformin potentiates anti-tumor effect of resveratrol on pancreatic cancer by down-regulation of VEGF-B signaling pathway, Oncotarget, 7, pp. 84190-84200 (Year: 2016).*
International Search Report issued for PCT/US2019/051354, mailed Jan. 2, 2020.
Liu et al., Identification of an annonaceous acetogenin mimetic, AA005, as an AMPK activator and autophagy inducer in colon cancer cells, PLoS One, vol. 7, No. 10, p. 8, 2012.
Li et al., Combined inhibition of glycolysis, the pentose cycle, and thioredoxin metabolism selectively increases cytotoxicity and oxidative stress in human breast and prostate cancer, Redox Biology, vol. 4, p. 127-135, 2015.

* cited by examiner trans-Gnetin H trans-ε-Viniferin

Gnetin C

ANTICANCER FORMULATION

RELATED APPLICATIONS

This application is a National Stage of International Application No. PCT/US2019/051354, filed Sep. 16, 2019, which claims priority from U.S. Provisional Patent Application No. 62/731,586 filed on Sep. 14, 2018, the entire disclosure of which is incorporated herein by this reference.

TECHNICAL FIELD

The presently-disclosed subject matter relates to anti-cancer compositions, methods of using compositions for cancer treatment, type-2 diabetes, and other metabolic conditions related to type-2 diabetes.

BACKGROUND

In efforts to identify more targeted and less toxic approaches for cancer therapy recent research has increasingly focused on the metabolic differences exhibited by cancer cells (1). Especially relevant is the enhanced use of glycolysis by cancer cells for both ATP production and metabolic building blocks to support cell proliferation. In practice however, upon treatment with agents that inhibit various aspects of glycolysis, cancer cells will adapt by enhancing use of mitochondrial oxidative phosphorylation to meet energy needs. Investigators have met this adaptation by employing agents that target oxidative phosphorylation using mitochondrial complex I inhibitors such as metformin or phenformin in combination with compounds that inhibit glycolysis. For example, combinations used include metformin plus the lactate dehydrogenase inhibitor oxamate (2) phenformin plus oxamate (3), metformin plus the hexokinase inhibitor 2-deoxyglucose (4), or metformin plus the pyruvate dehydrogenase kinase inhibitor dichloroacetate (5, 6), The use of combinations of these agents in vitro results in synergistic cell apoptosis and in various mouse tumor models, dramatic reductions in tumor growth (2-6). However, in cancer cells lacking functional p53, these combinations do not induce apoptosis but rather result in cell cycle arrest in G2-M in an additive fashion (7). In the continuing endeavor for less toxic and more targeted cancer therapy, it would be advantageous to identify synergistically cytotoxic compositions that induce apoptosis in cancer cells. In addition, the present inventors have determined that the anticancer agent described impacts a target important for type-2 diabetes and related metabolic disorders and thus could be a therapeutically relevant intervention.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

FIGS. 2 A-C. show GH inhibits lactic acid production.

Figure 22A:
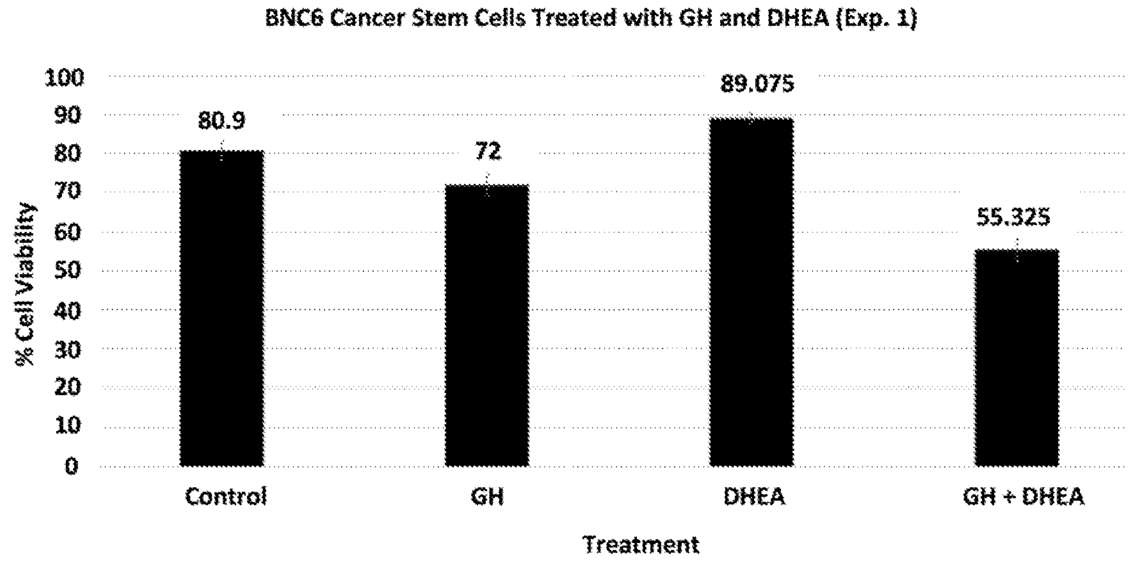
Figure 22B:
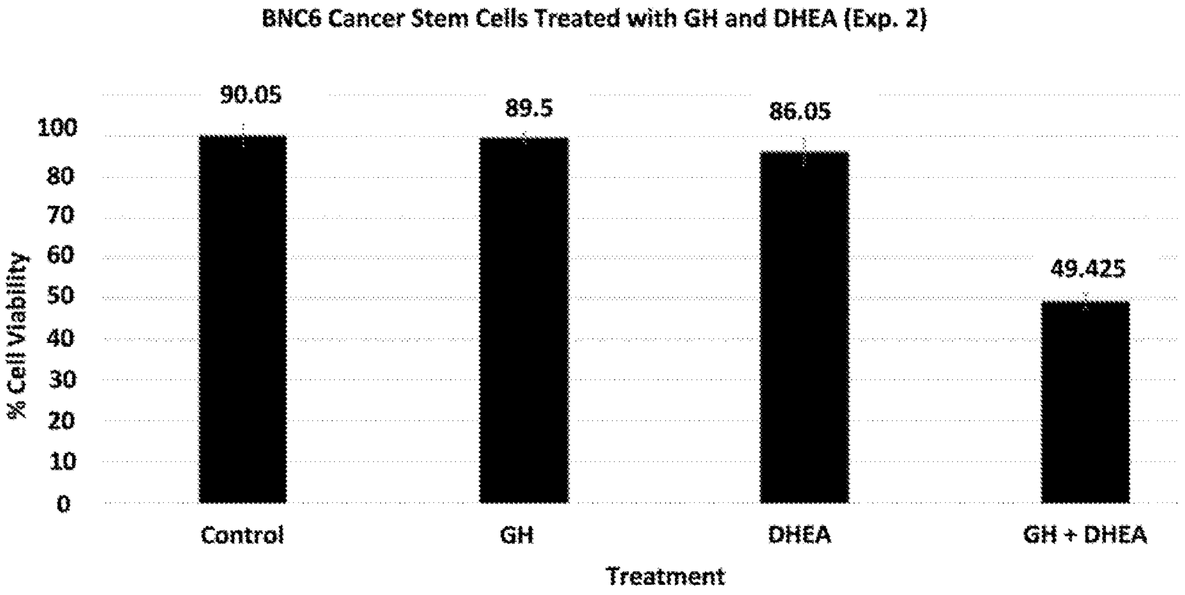

FIGS. 22 A-B. shows a graphic representation from two separate experiments of the percentage of cell viability as determined by Trypan Blue exclusion cell count that indicates that GH (a glycolysis inhibitor) in combination with DHEA (a glucose-6-phosphate dehydrogenase inhibitor) is cytotoxic to cancer stem cells (CSCs) grown from BNC6 patient derived Glioblastoma cells and in 24 h induces substantial cell death. A. first experiment, B. Second experiment.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently—disclosed subject matter.

Unless defined otherwise, all technical and scientific terms used herein have the same meaning as is commonly understood by one of skill in the art to which the invention(s) belong.

All patents, patent applications, published applications and publications, databases, websites and other published materials referred to throughout the entire disclosure herein, unless noted otherwise, are incorporated by reference in their entirety.

Although any methods, devices, and materials similar or equivalent to those described herein can be used in the practice or testing of the presently-disclosed subject matter, representative methods, devices, and materials are described herein.

The presently-disclosed subject matter meets some or all of the above-identified needs, as will become evident to those of ordinary skill in the art after a study of information provided in this document. To avoid excessive repetition, this Description does not list or suggest all possible combinations of such features.

Mention of one or more representative features of a given embodiment is likewise exemplary. Such an embodiment can typically exist with or without the feature(s) mentioned; likewise, those features can be applied to other embodiments of the presently-disclosed subject matter, whether listed or not.

Disclosed herein are compositions for the treatment of cancer. Compositions including trans-Gnetin H (GH), which is a potent in vitro glycolysis/lactic acid production inhibitor, when used in combination with mitochondrial complex I inhibitors are synergistically cytotoxic and unexpectedly induce apoptosis in cancer cells and cancer stem cells containing either wild type or dysfunctional p53. The surprising effect in cells with dysfunction p53 suggests that GH, in addition to inhibiting glycolysis/lactic acid production, impacts an additional target or targets that results in the synergistic induction of apoptosis in cells lacking functional p53.

One embodiment of the present invention relates to a composition comprising: a glycolysis inhibitor, and a mitochondrial complex I inhibitor or glucose-6-phosphate dehydrogenase inhibitor. In some embodiments the glycolysis inhibitor is gnetin H (GH). In other embodiments of the invention, the GH is trans-GH. In some embodiments of the present invention, GH is derived from a plant. In some embodiments of the present invention, the plant is of the genus *Paeonia.*

In some embodiments of the present invention, the glucose-6-phosphate dehydrogenase inhibitor is DHEA.

In other embodiments of the present invention, the mitochondrial complex I inhibitor is selected from the group metformin, phenformmin, rotenone, piericidinA, and acetogenins. In some embodiments, the mitochondrial complex I inhibitor is acetogenins. In other embodiments, the acetogenins is derived from a plant. In other embodiments of the present invention, the plant is of the genus *Asimina.*

One embodiment of the present invention relates to a method of treating metabolic disorders comprising administering to a subject a therapeutically effective amount of a glycolysis inhibitor, and a mitochondrial complex I inhibitor or glucose-6-phosphate dehydrogenase inhibitor. In further embodiments, the metabolic disorder is selected from cancer, type 2 diabetes, glycolysis related disorder, or a disorder causing reduced lactic acid production. In other embodiments of the present invention, the subject is a mammal or a human. In some embodiments of the present invention, the subject has functional p53 or dysfunctional p53. In further embodiments of the present invention, the metabolic disorder is cancer and administration of the composition reduces tumor growth or tumor burden or a combination thereof. In other embodiments of the present invention, the administration is oral, transdermal, nasal, intracerebral, or by injection.

Another embodiment of the present invention relates to a method of inhibiting the proliferation of cancer cells comprising, administering a therapeutically effective amount of GH and a mitochondrial complex I inhibitor or a glucose-6-phosphate dehydrogenase inhibitor to a subject in need thereof. In further embodiments, the cancer cells are cancer stem cells. In some embodiments, the administered amount of GH would result in tissue levels from about 1 micromolar to about 10 micromolar. In other embodiments of the present invention, the subject has functional p53 or dysfunctional p53. In further embodiments of the present invention, the administration of the composition reduces tumor growth or tumor burden or a combination thereof. In other embodiments of the present invention, the subject is a mammal or a human. In other embodiments of the present invention, the administration is oral, transdermal, nasal, intracerebral, or by injection. In further embodiments of the present invention, the proliferation of cancer cells are inhibited via apoptosis. In further embodiments of the present invention, the cancer cells are selected from glioblastoma, melanoma, sarcoma, cervical carcinoma, ovarian carcinoma, colo-rectal cancer, lung cancer, head & neck cancer, prostate cancer, pancreatic cancer, and breast cancer.

The mitochondrial complex I inhibitor of the presently disclosed composition can include natural product inhibitors such as rotenone, piericidin A, Rolliniastatin 1 and 2, Stigmatellin, Mucidin, and Capsaicin. In some embodiments, the inhibitor is selected from metformin, phenformin, and acetogenins. In some embodiments, the inhibitor is an acetogenin that is an extract from Paw Paw. In some embodiments, the extract is from Paw Paw twigs. The mitochondrial complex I inhibitor is not limited by a particular structure, and mitochondrial complex I inhibitors are well-known in the art. (8)

A method of treating cancer is disclosed herein and comprises administering a composition of the presently-disclosed subject matter. In some embodiments, the method administers the composition to cancer cells with functional or dysfunctional p53. In some embodiments, the composition is administered to cancer cells or cancer stem cells. In some embodiments, the cancer cells are from a human or a mouse. In some embodiments, the cancer cells are glioblastoma, breast cancer, melanoma, osteosarcoma, cervical carcinoma, or ovarian carcinoma. In some embodiments, the administering reduces cell survival. In some embodiments, the composition results in a synergistic anti-proliferative effect relative to the administration of the GH and mitrochondrial complex I inhibitor alone. In some embodiments, the method reduces tumor growth. Methods of inhibiting lactic acid production, and/or glycolysis are also disclosed herein, and comprise administering GH to a subject. The GH can be administered, optionally, with a mitochondrial complex I inhibitor, and can also be administered alone.

Regarding the concentration of the GH of the composition, in some embodiments, the GH is present at a concentration of about 1 micromolar to about 100 micromolar. In some embodiments, more preferably, the GH is provided at a concentration of about 1 to about 20 micromolar, or 1, 2, 3, 4, 5, 6, 7, 8 or about 9 micromolar.

In some embodiments, the composition is administered based on the weight of the subject. In some embodiments, for example, the GH in the composition is provided at about 0.1 mg/Kg to about 100 mg/Kg, in some embodiments, about 0.5 to about 20 mg/Kg, about 1 to 5 mg/Kg, or about 1.5 mg/Kg to a subject per day. In some embodiments, the GH is provided as PSE, which is provided at an amount of about 1 to about 20 mg/Kg, 1 to 10 mg/Kg. In some embodiments, the mitochondrial complex inhibitor is provided at an amount of 0.1 to about 1.5 mg/Kg per day. In some embodiments, the inhibitor is an acetogenin is provided at 0.5 mg/Kg in a subject.

In some embodiments, the composition induces synergistic cytotoxicity. In this regard, the GH when administered with a mitochondrial complex I inhibitor provides an additive anti-proliferative effect. In some embodiments, the anti-proliferative effect can be measured based on percent cell survival when administered in combination relative to when administered alone. In some embodiments, the anti-proliferative effect can be measured based on the progression of tumor growth and/or tumor burden.

The term "administering" refers to any method of providing a GH and mitochondrial I inhibitor and/or pharmaceutical composition thereof to a subject. Such methods are well known to those skilled in the art and include, but are not limited to, oral administration, transdermal administration, nasal administration, intracerebral administration, and administration by injection, which itself can include intravenous administration, intra-arterial administration, intramuscular administration, subcutaneous administration, intravitreous administration, intracameral (into anterior chamber), and intraperitoneal administration, and the like. Administration can be continuous or intermittent. In various aspects, a preparation can be administered therapeutically; that is, administered to treat an existing disease or condition (e.g., ischemia, infarction, etc.). In other instances a preparation is administered prophylactically; that is, administered to prevent or treat a disease or condition that may otherwise develop. In some embodiments, the administration is intra-arterially, intraperitoneally, or intravenously.

As used herein, the terms "effective amount" and "therapeutically effective amount" are used interchangeably and mean a dosage sufficient to provide treatment. The exact amount that is required will vary from subject to subject, depending on the species, age, and general condition of the subject, the particular carrier or adjuvant being used, mode of administration, and the like. As such, the effective amount will vary based on the particular circumstances, and an appropriate effective amount can be determined in a particular case by one of ordinary skill in the art using only routine experimentation.

In some instances an effective amount is determined relative to the weight of a subject, and can be selected from dosages of about 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg, 31 mg/kg, 32 mg/kg, 33 mg/kg, 34 mg/kg, 35 mg/kg, 36 mg/kg, 37 mg/kg, 38 mg/kg, 39 mg/kg, 40 mg/kg, 41 mg/kg, 42 mg/kg, 43 mg/kg, 44 mg/kg, 45 mg/kg, 46 mg/kg, 47 mg/kg, 48 mg/kg, 49 mg/kg, and 50 mg/kg.

The term "subject" is used herein to refer to a target of administration, which optionally displays symptoms related to a particular disease, pathological condition, disorder, or the like. Thus, in some embodiments a subject refers to a target that displays symptoms of ischemia and/or infarction. The subject of the herein disclosed methods can include both human and animal subjects. A subject can be, but is not limited to, vertebrates, such as mammals, fish, birds, reptiles, or amphibians. More specifically, the subject of the herein disclosed methods can include, but is not limited to, a human, non-human primate, cat, dog, deer, bison, horse, pig, rabbit, dog, sheep, goat, cow, cat, guinea pig, or rodent. The term does not denote a particular age or sex. Adult and newborn subjects, as well as fetuses, whether male or female, are intended to be covered. The term "subject" includes human and veterinary subjects.

The terms "treat," "treatment," and the like refer to the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative (prophylatic) treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

While the terms used herein are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter is further illustrated by the following specific but non-limiting examples. The following examples may include compilations of data that are representative of data gathered at various times during the course of development and experimentation related to the present invention.

EXAMPLES

Figure 1:
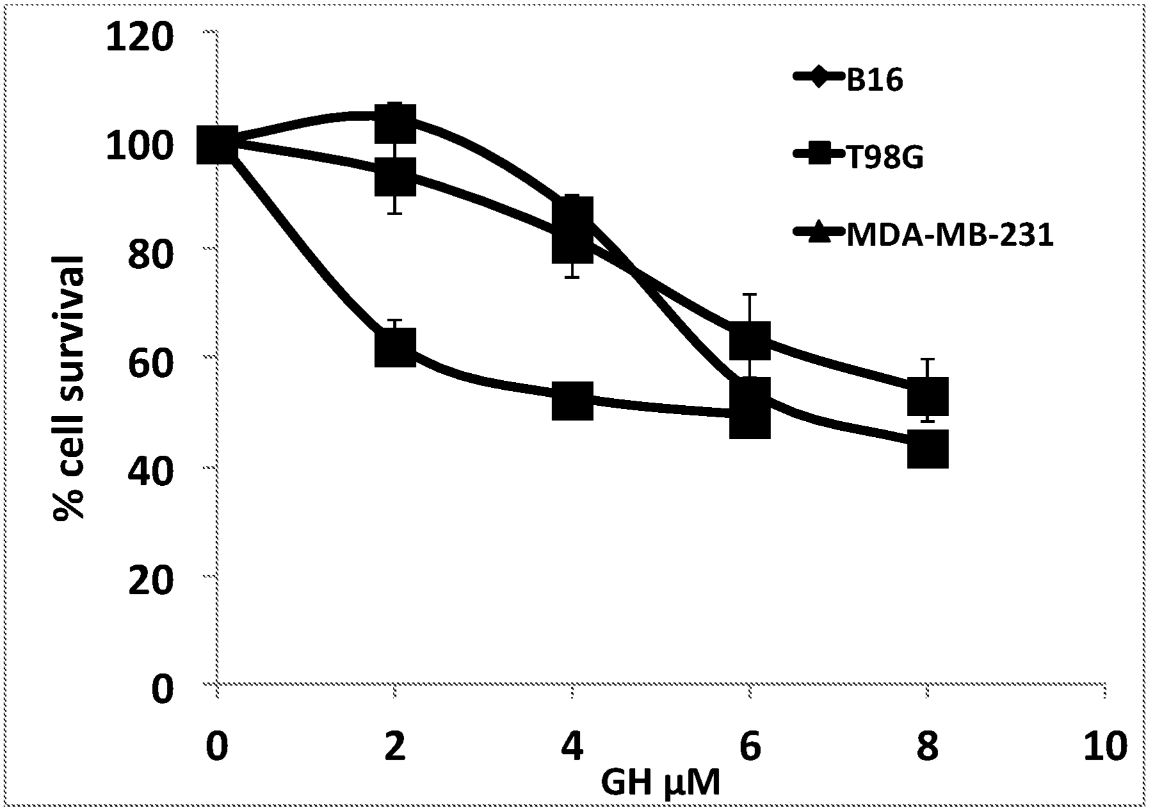
FIG. 1 shows Trans-Gnetin H inhibits cell proliferation.

Example 1: trans-Gnetin H (GH)—Trans-Gnetin H inhibits cell proliferation. FIG. 1 shows that trans-Gnetin H (GH), similar to the anti-proliferative action of other oligo stilbenes (9), inhibits the proliferation of several cancer cell lines in a dose dependent fashion. B16 mouse melanoma cells, T98G glioblastoma cells, and MDA-MB-231 human breast cancer cells were treated with varying concentrations of GH for 48 hours with cell survival measured. The B16 mouse melanoma cell line was the most sensitive to the anti-proliferative action of GH, perhaps due to the highly glycolytic nature of these cells and/or that they contain wild type p53.

Figure 2A:
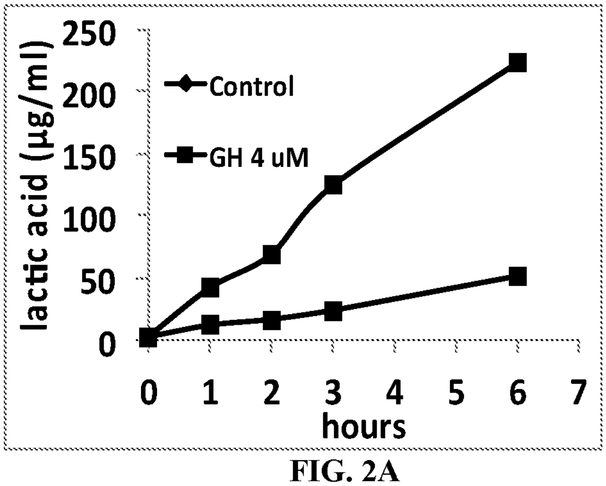
FIG. 2A shows B16 mouse melanoma cells.
Figure 2B:
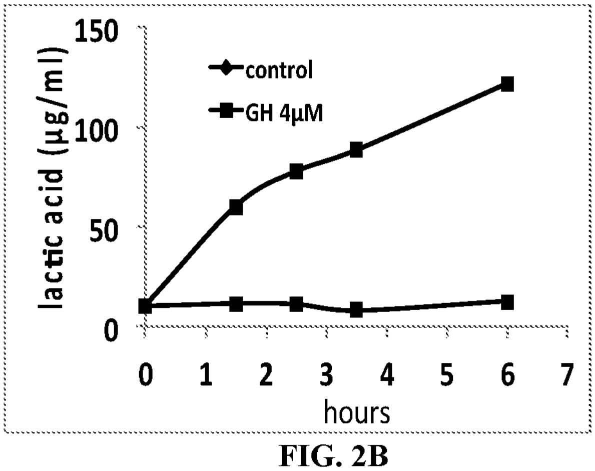
FIG. 2B shows T98G human glioblastoma cells.
Figure 2C:
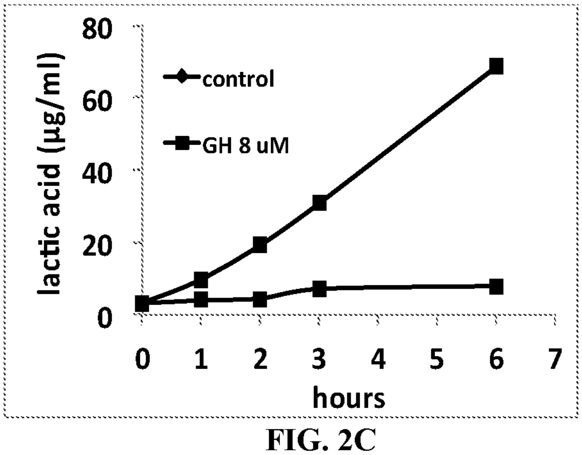
FIG. 2C shows MDA-MB-231 human breast cancer cells.

GH inhibits lactic acid production. During cell survival experiments the acidification of the cell culture medium was inhibited when GH was present. Acidification of the cell culture medium occurs because of the enhanced use of glycolysis by transformed cells (and resulting increase in lactic acid production). This led us to investigate whether GH reduced lactic acid levels in the cell culture medium. FIGS. 2 A-C. shows that GH inhibits the accumulation of lactic acid in the medium of several human and mouse cancer cell lines.

Figure 3A:
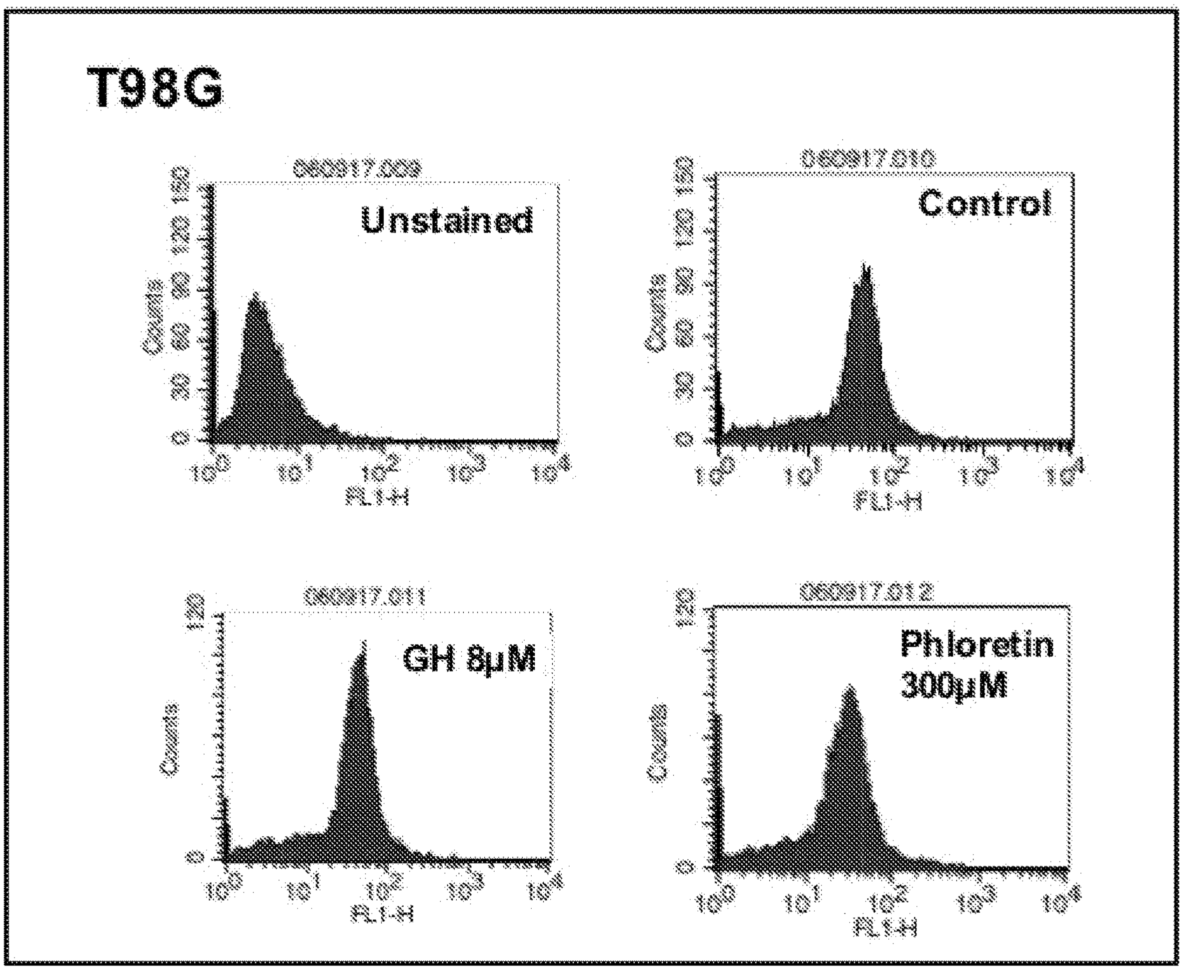
FIGS. 3 A-C. show GH does not inhibit glucose transport.
Figure 3B:
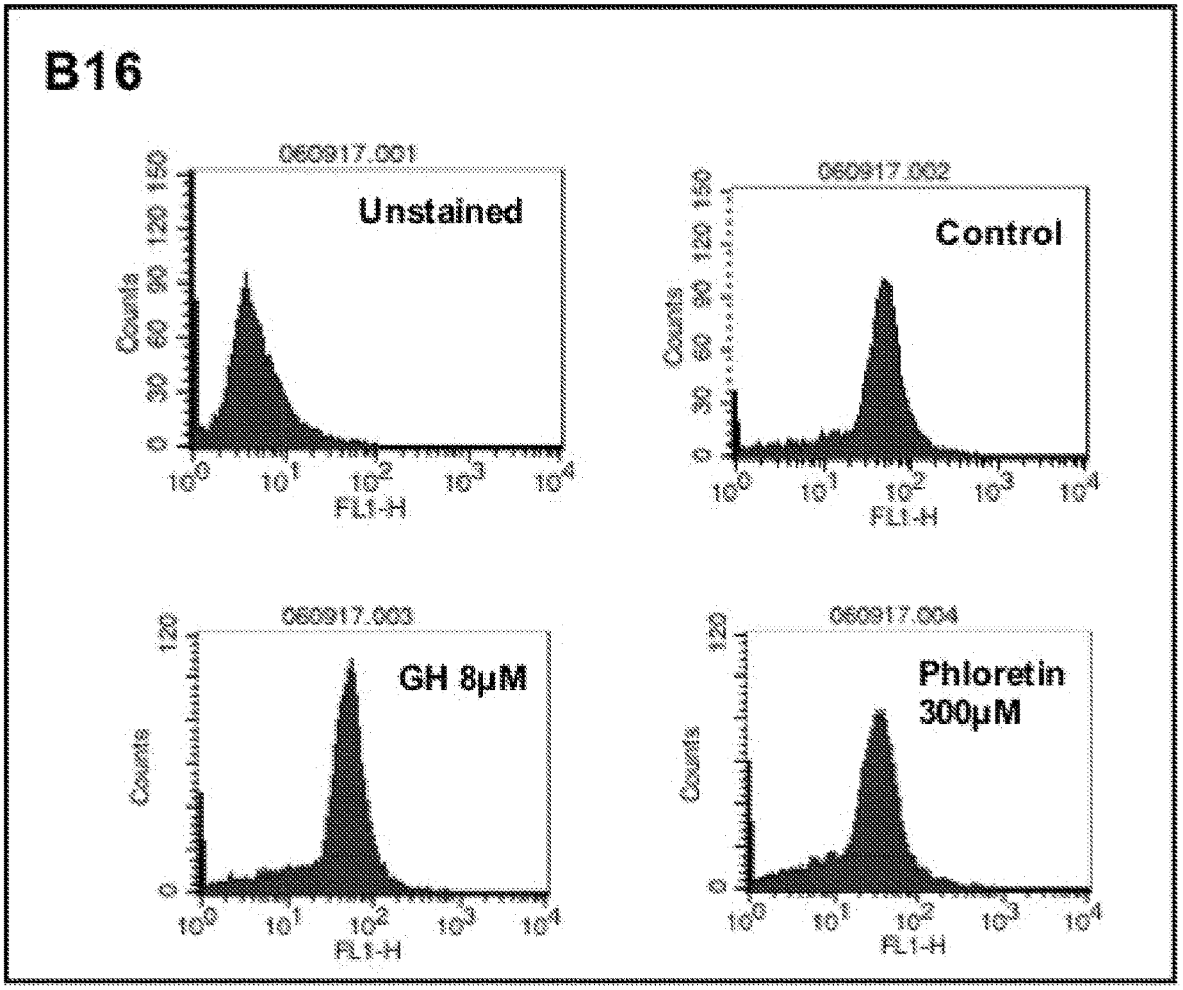
Figure 3C:
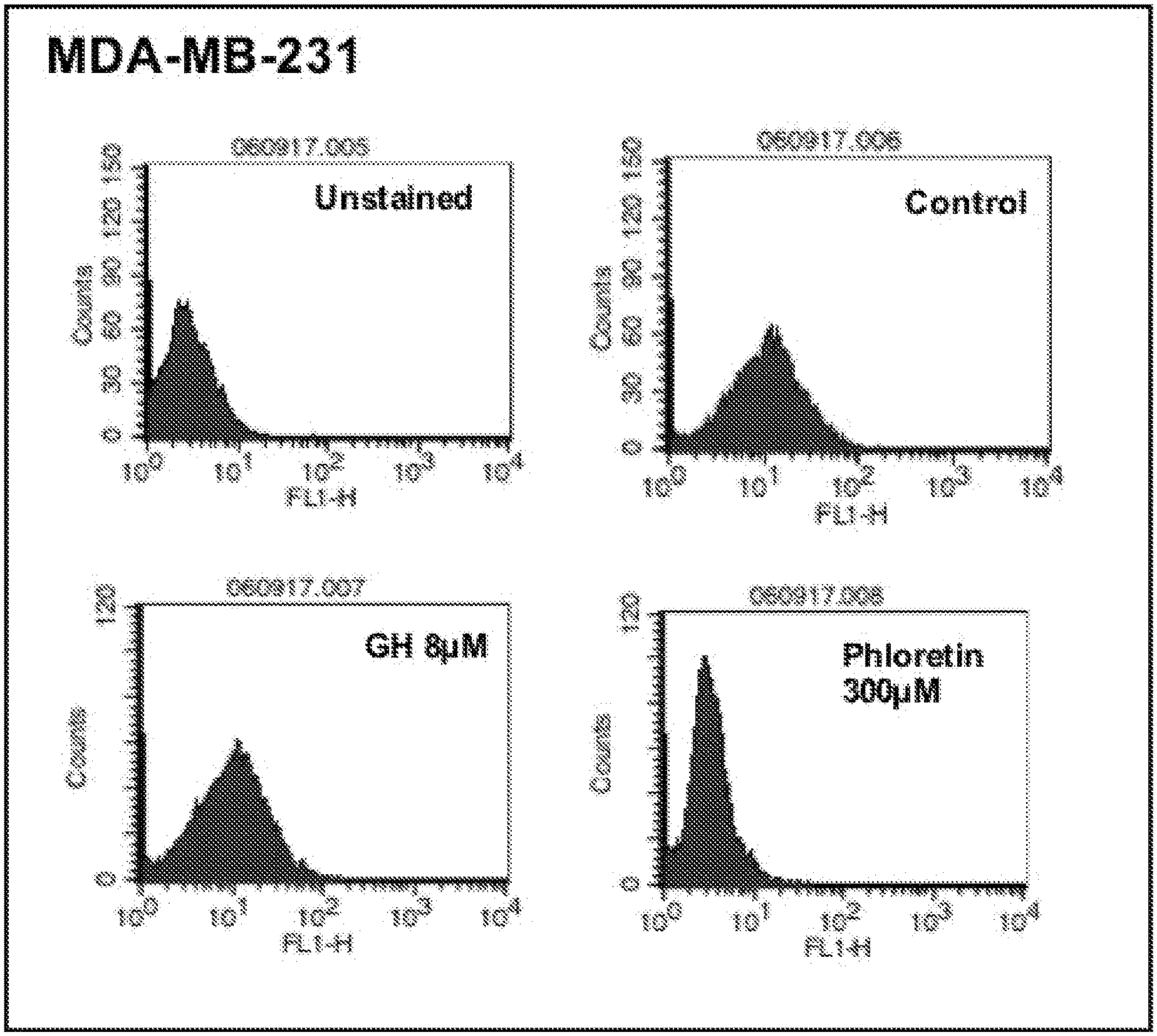

GH does not inhibit glucose transport. Since the inhibition of the accumulation of lactic acid in the medium occurred rapidly it suggested that either GH inhibited the transport of glucose across the cell membrane, that it inhibited an enzymatic step in glycolysis or that it inhibited lactic acid efflux from the cell. FIGS. 3 A-C. suggests that GH does not inhibit glucose transport across the cell membrane of these three cell lines since GH did not influence the accumulation of fluorescently labeled 2-deoxy-2-[(7-nitro-2,1,3-benzoxadiazol-4-yl)amino]-D-glucose (2-NBDG). Phloretin, a known glucose transport inhibitor, was used as a positive control. Accumulation of 2-NDGB was inhibited by phloretin by 54% in T98G cells, by 31% in B16 cells and by 74% in MDA-MB-231 cells. The first panel for each cell line represents unstained cells, the second stained with 2-NBDG for one hour, the third treated with GH for one hour followed by 2-NBDG for one hour and the fourth treated with phloretin for one hour followed by 2-NBDG for one hour.

Figure 4:
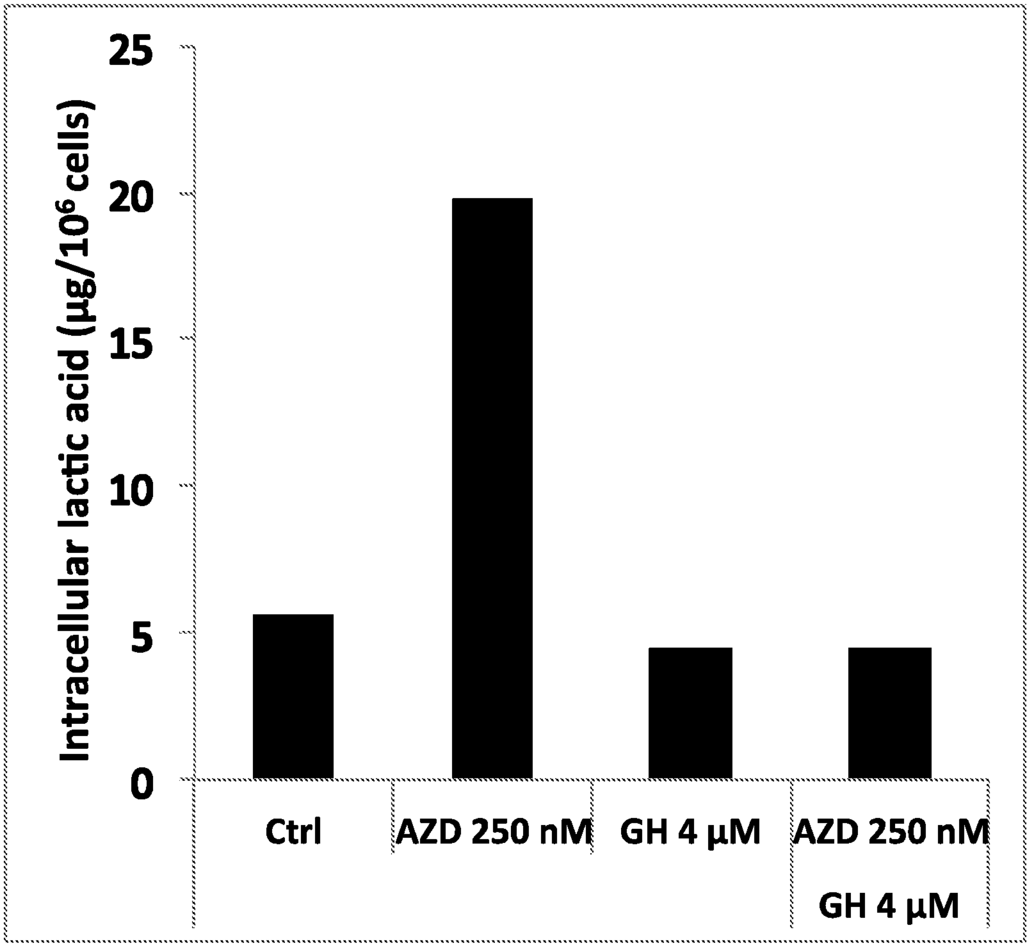
FIG. 4 shows GH does not inhibit lactic acid export from the cell.

GH does not inhibit lactic acid export from the cell. To prevent the buildup of lactic acid within the cell a family of monocarboxylate transporters (MCT) functions to transport lactic acid out of the cell (10). To determine if GH inhibits lactic acid export from the cell, and in this manner inhibits the accumulation of lactic acid in the cell culture medium, intracellular lactic acid levels were measured. If GH inhibited lactic acid export, treatment of cells with GH would result in the increase in intracellular lactic acid levels. As a positive control the MCT1 inhibitor AZD3965 was used. FIG. 4 shows that treatment of B16 cells with AZD3965 for 3 hours results in the substantial accumulation of intracellular lactic acid (~4-fold above control values) while treatment with GH did not increase intracellular lactic acid. Furthermore, treatment with AZD3965 plus GH did not result in the accumulation of intracellular lactic acid. The lack of lactic acid accumulation under this combination treatment suggests that GH blocked the synthesis of lactic acid and therefore it could not accumulate in the presence of the inhibitor of the MCT1 lactic acid exporter (AZD3965). Together these results indicate that GH does not inhibit lactic acid export from the cell but instead they suggest that GH inhibits the synthesis of lactic acid.

Figure 5:
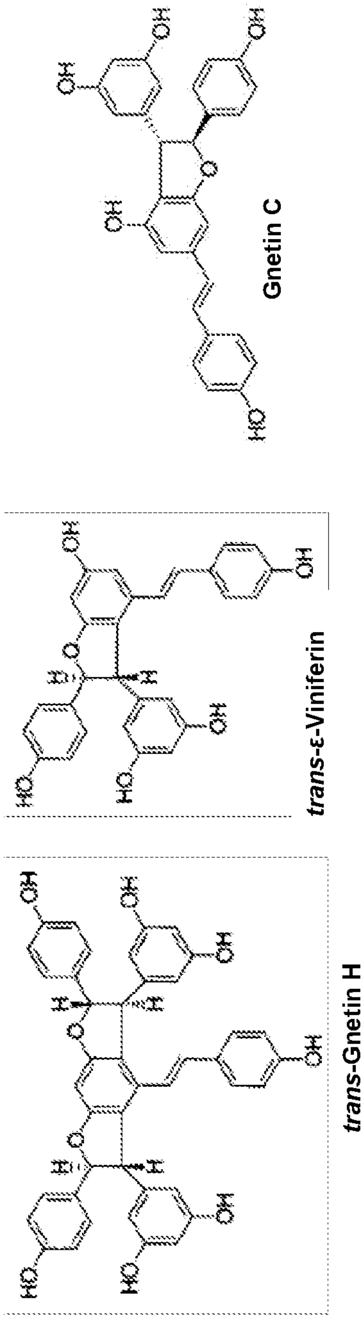
FIG. 5 shows the structures of trans-GH, trans-E-Viniferin (Vin), and Gnetin C.

Another oligo stilbene also inhibits lactic acid production. GH is a trimer of resveratrol-like (stilbene) compounds. These oligo stilbenes can be found naturally as dimers, trimers, etc. Several oligo stilbenes, GH, trans-ε viniferin (Vin), gnetic C (GC) (FIG. 5) were tested at different concentrations for their ability to inhibit lactic acid accumulation over a three hour period using T98G human glioblastoma cells.

Figure 6:
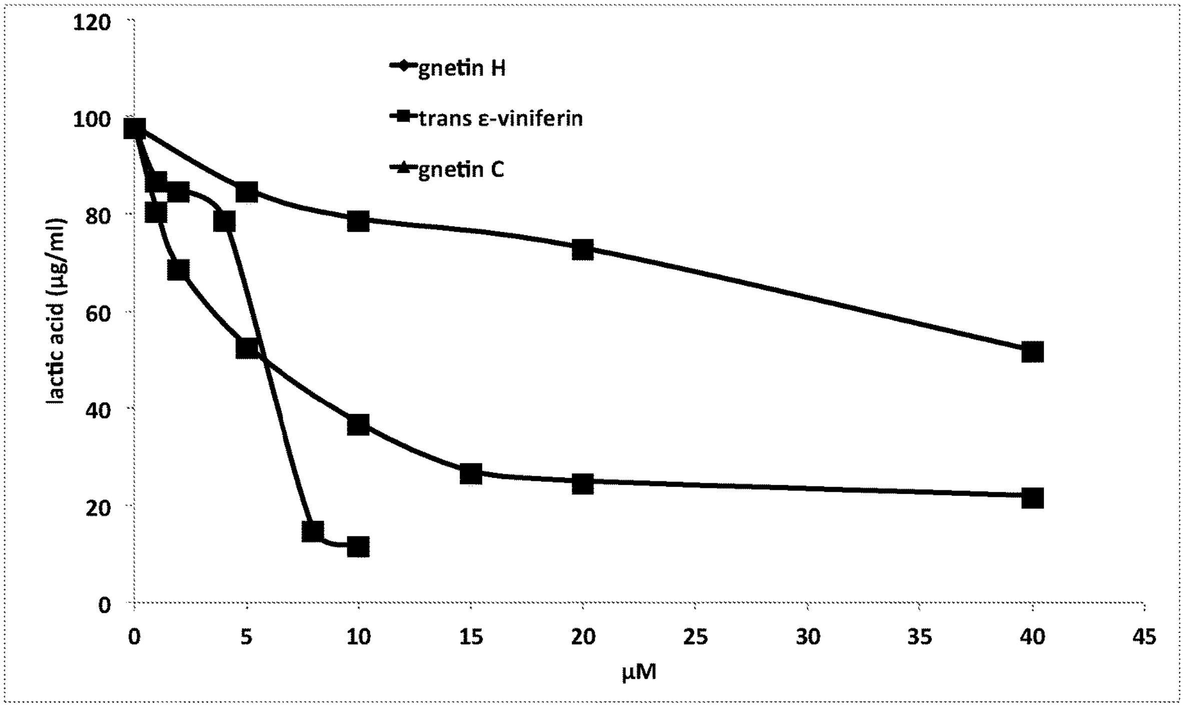
FIG. 6 shows CG and to a lesser extent, Vin, inhibit lactic acid.
Figure 7:
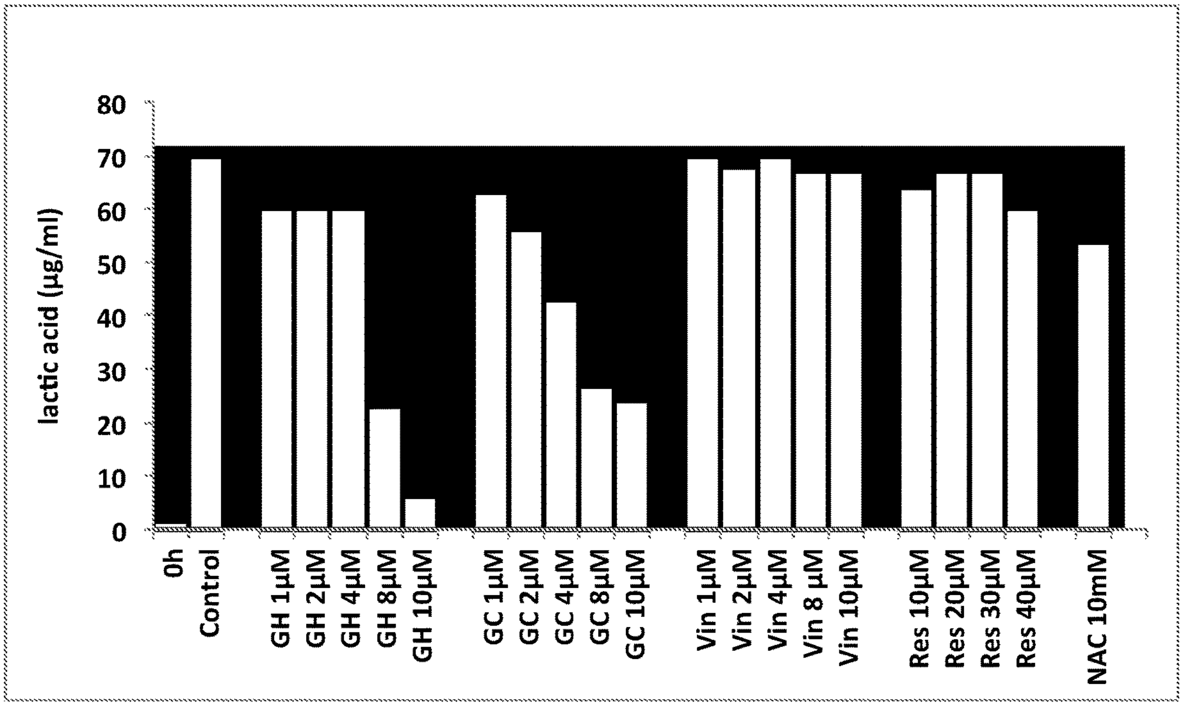
FIG. 7 shows Resveratrol (Res) and n-acetylcysteine (NAC) did not inhibit lactic acid production.

FIG. 6 demonstrates that while GC also potently inhibited lactic acid production, Vin was less potent and 40 μM was required to inhibit lactic acid production by 40%. Resveratrol (Res) and n-acetylcysteine (NAC) were also investigated, but did not inhibit lactic acid production (FIG. 7).

Figure 8:
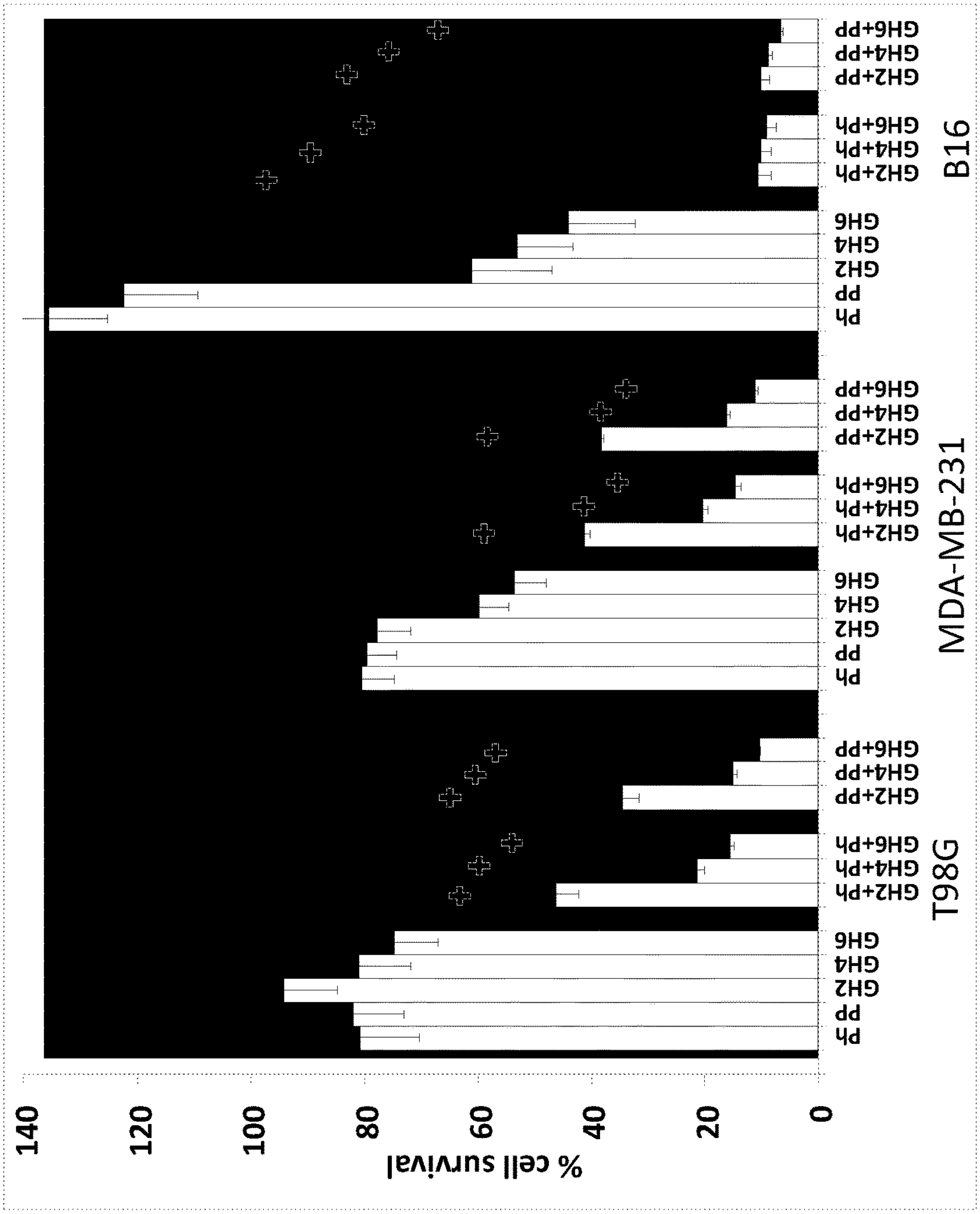
FIG. 8 shows GH is synergistically cytotoxic in combination with mitochondrial complex I inhibitors.

Example 2: Gnetin H In Combination with Mitochondrial Complex I Inhibitors. GH is synergistically cytotoxic in combination with mitochondrial complex I inhibitors. During investigation of the possible synergistic action between identified anti-proliferative natural products, GH, but not 10 other tested natural products (data not shown), was synergistically cytotoxic with mitochondrial complex I inhibitors. FIG. 8 demonstrates that GH (numbers indicate concentration in μM) was synergistically cytotoxic when combined with phenformin (Ph) at 100 μM or the natural product (11) acetogenins (PP) mitochondrial complex I inhibitor at 1 μg/ml (acetone extract from Paw Paw twigs). The plus signs above the combination treatment bars indicates the value of % cell survival if the anti-proliferative effect was additive. Since the bar values are substantially below the plus signs, these combination treatments all resulted in a synergistic anti proliferative effect. In addition to these three cell lines, GH was synergistically cytotoxic with phenformin on BT-549, SK-MEL, KHOS, KB (HeLa), and SK-OV3 (data not shown).

Figure 9A:
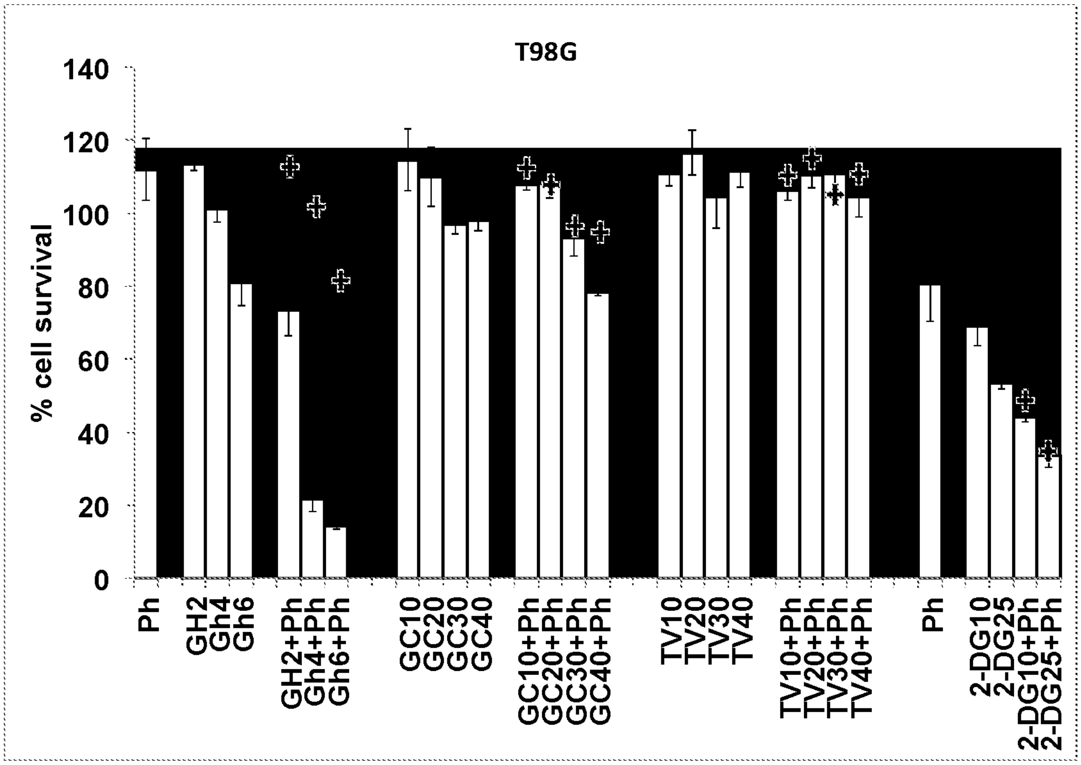
FIGS. 9 A-B. show GC does not synergize with mitochondrial complex I inhibitors.
Figure 9B:
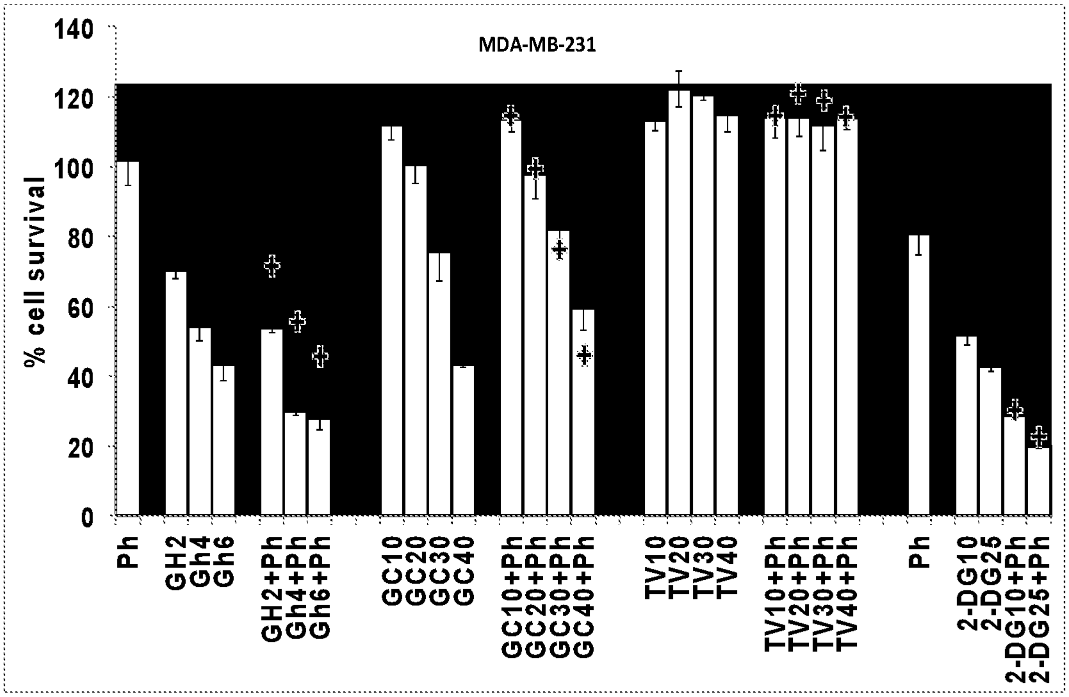

GC does not synergize with mitochondrial complex I inhibitors. Since both GH and GC potently inhibited lactic acid production it was investigated whether GC inhibited proliferation and whether it was synergistically cytotoxic when combined with a mitochondrial complex I inhibitor. FIGS. 9 A-B. shows that even though GC was a potent inhibitor of lactic acid production it did not substantially inhibit proliferation in T98G cells when used alone and it was not synergistically cytotoxic when combined with phenformin (Ph) at 100 μM.

Figure 10:
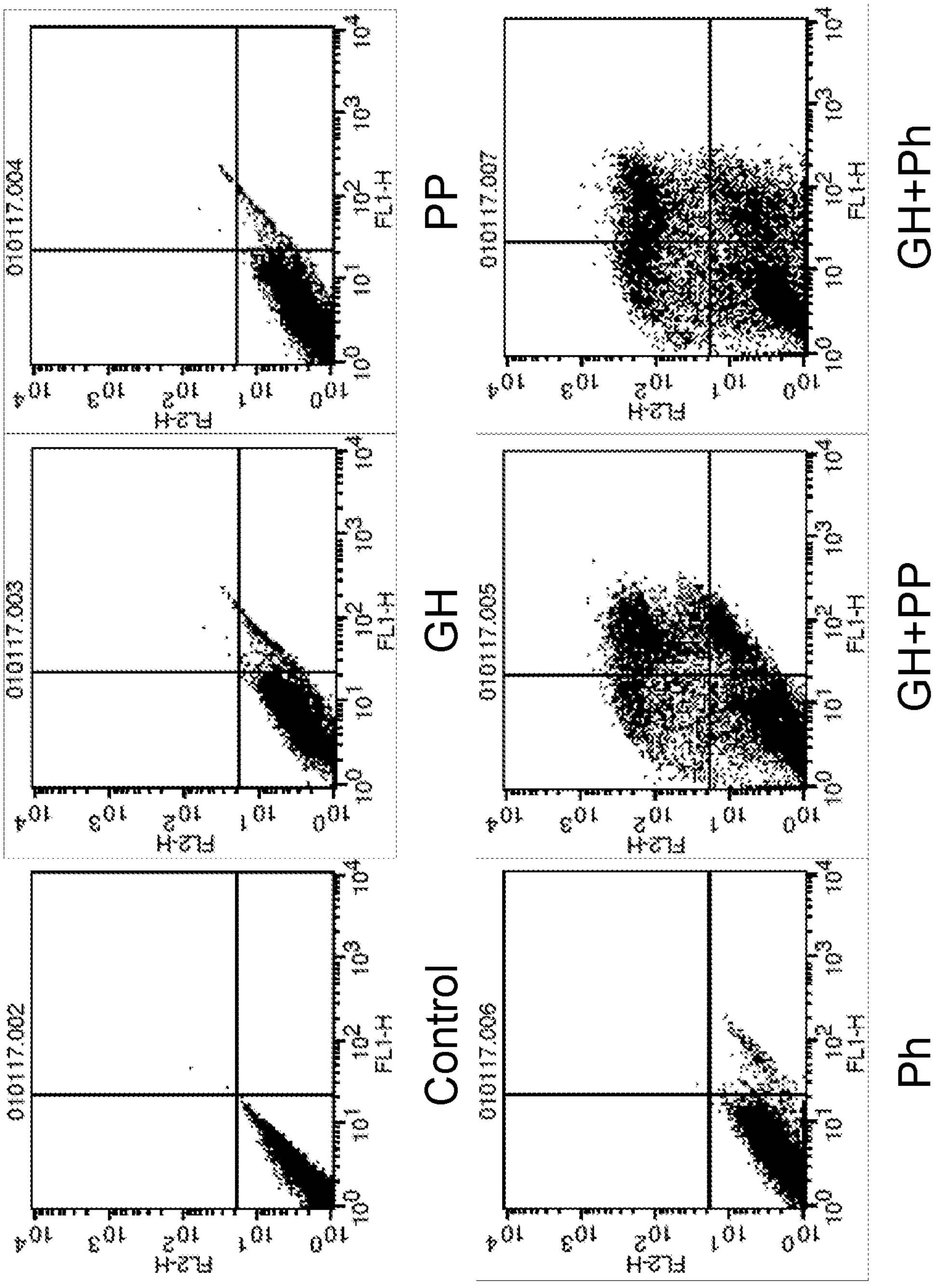
FIG. 10 shows the combination of GH with phenformin (Ph) or the Paw Paw extract (PP) results is extensive induction of apoptosis in T98G cells using annexin V/propidium iodide (PI) staining.

In FIGS. 9 A-B., the plus signs are placed above the combination treatment bars at the % cell survival value if the anti-proliferative effect was additive. Since the top of the combination treatment bars are co-located with the plus signs all treatments except GH plus Ph were additive. Similarly, trans-ε viniferin (TV) did not mimic GH activity. Similar results were also seen using MDA-MB-231 human breast cancer cell line. Numbers after GH, GC and TV indicate concentration in μM while those after 2-DG indicate concentration in mM. Consistent with published reports using p53 deficient cells (7), co treatment with the glycolysis inhibitor 2-deoxyglucose (2-DG) and mitochondrial complex I inhibitor was not synergistically cytotoxic (FIGS. 9 A-B.) and published studies showed that these combinations do not induce apoptosis but rather result in cell cycle arrest in G2-M (7). Both T98G and MDA-MB-231 cells lack functional p53 but B16 are p53 wild type. This suggests that GH influences another cellular target in addition to inhibition of lactic acid production that results in synergistic cytotoxicity when combined with mitochondrial complex I inhibitors in p53-deficient cells. This additional target remains to be identified. Alternatively, without being bound by theory, the mechanisms by which GH and GC inhibit lactic acid production may differ and this may be responsible for their differential action on proliferation and cytotoxicity. FIG. 10 demonstrates that the combination of GH with phenformin (Ph) or the Paw Paw extract (PP) results is extensive induction of apoptosis in T98G cells using annexin V/propidium iodide (PI) staining.

Figure 11:
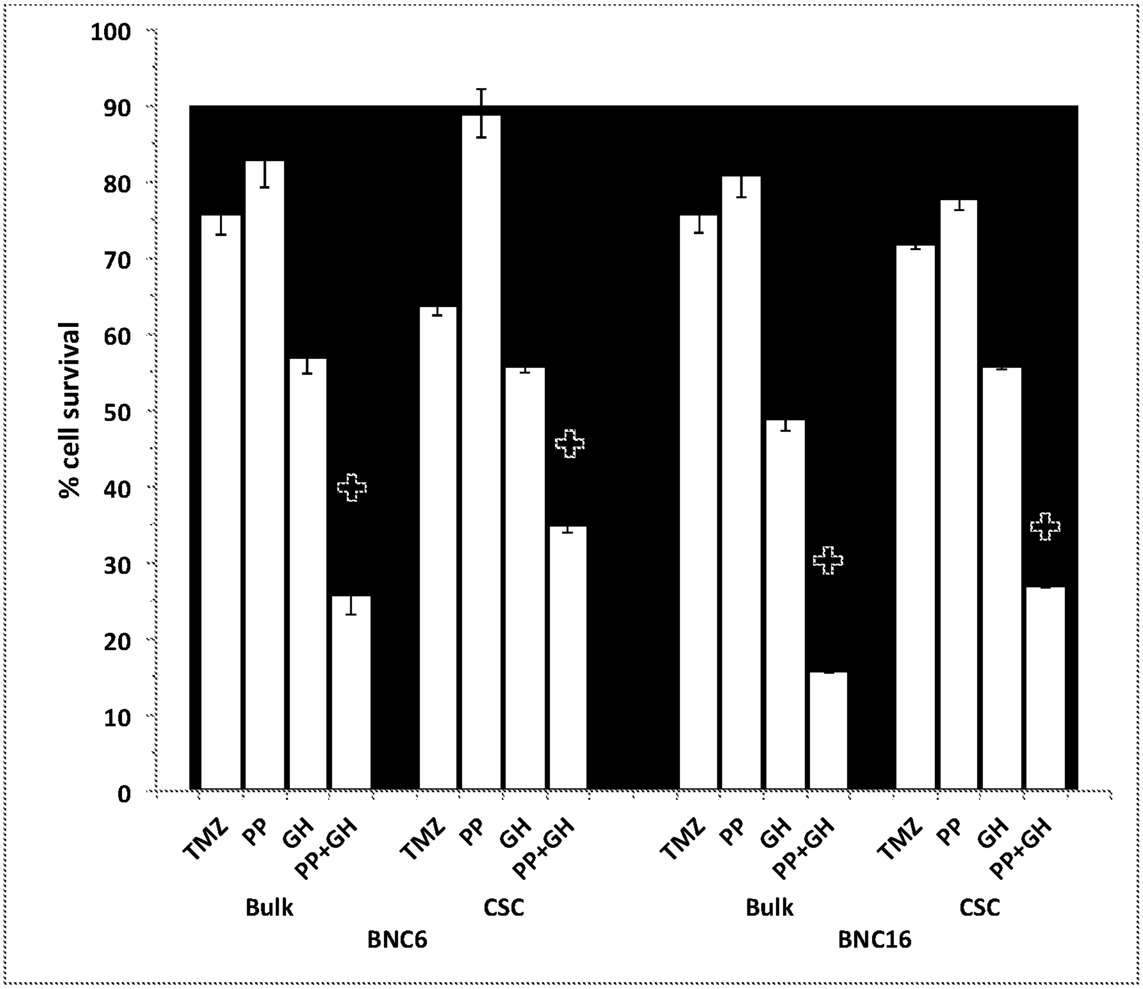
FIG. 11 shows GH (4 μM) in combination with a mitochondrial complex I inhibitor is synergistically cytotoxic using patient derived bulk and cancer stem cell populations from glioblastoma.

Example 3: Paw Paw Extract. GH (4 μM) in combination with a mitochondrial complex I inhibitor is synergistically cytotoxic using patient derived bulk and cancer stem cell populations from glioblastoma. GH and acetogenin extract from Paw Paw (PP-2 μg/ml) were synergistically cytotoxic when using bulk tumor cells and cancer stem cell (CSC) populations from two patients with Temodar (TMZ)-resistant glioblastoma (FIG. 11).

The plus signs are placed above the combination treatment bars at the % cell survival value if the anti-proliferative effect was additive. Since the top of the bars are substantially below the plus signs, these combination treatments all resulted in a synergistic anti proliferative effect. These results were similar to the synergistic cytotoxic action of this combination using the widely used Temodar-resistant glioblastoma cell line T98G (FIG. 8).

Figure 12A:
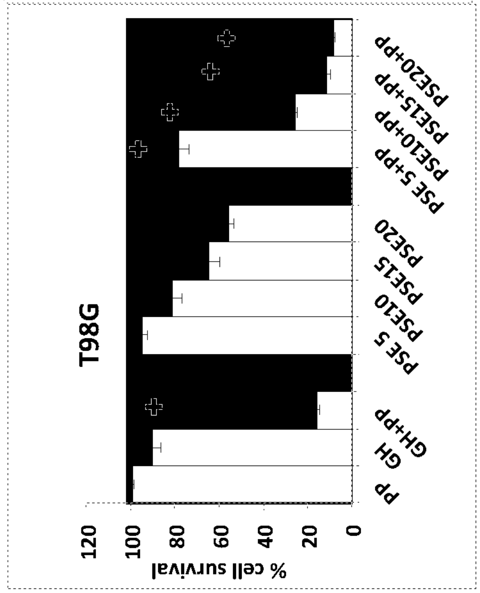
FIGS. 12 A-C show Peony seed extract (PSE) exhibits synergistic cytotoxicity when combined with a mitochondrial complex I inhibitor (Paw Paw acetogenins extract).
Figure 12B:
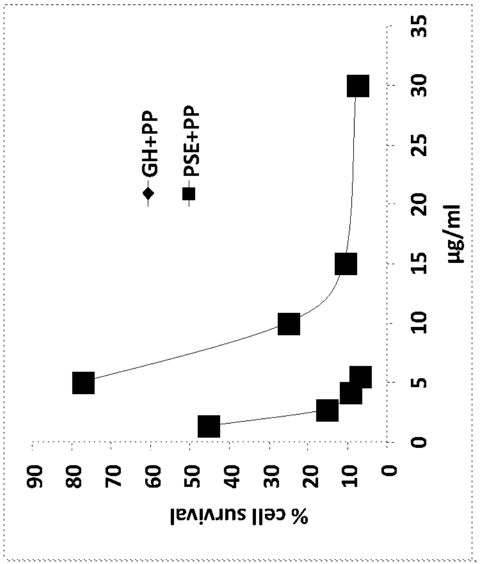
Figure 12C:
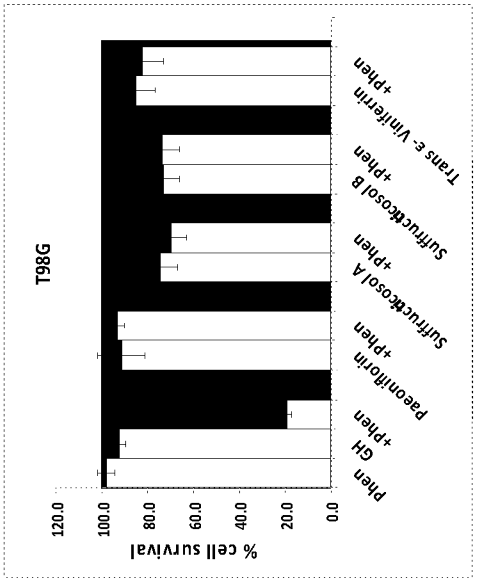

Example 4: Peony Seed extract. Peony seed extract (PSE) exhibits synergistic cytotoxicity when combined with a mitochondrial complex I inhibitor (Paw Paw acetogenins extract). T98G cells were treated with different concentrations of purified GH (numbers indicate μM) or PSE (numbers indicate μg/ml) alone or in combination with a Paw Paw (PP) extract (2 μg/ml) for 48 hrs (FIG. 12 A). The plus signs are placed above the combination treatment bars at the % cell survival value if the anti-proliferative effect was additive. Since the top of the bars are substantially below the plus signs, PSE, like GH, exhibited synergistic cytotoxicity in combination with a mitochondrial complex I inhibitor (Paw Paw extract-PP). T98G cells were treated with different concentrations of purified GH or PSE in combination with a Paw Paw extract (2 μg/ml) for 48 hrs (FIG. 12 B). The amount of GH in this PSE is 19% w/w. If synergistic cytotoxicity with PP is due solely to GH within the PSE, then 5.3-fold more of this extract on a weight basis should be required to obtain cell killing equal to that obtained with purified GH. $IC_{50}$s for GH and PSE in combination with PP were 1.3 and 7.4 μg/ml, respectively (FIG. 12 B), a 5.7-fold difference suggesting that GH was solely responsible for synergy. Further evidence that GH is the main component within the PSE responsible for synergistic cytotoxicity with a mitochondrial complex I inhibitor is presented in FIG. 12 C, GH (4 μM), but none of the other main components (at 30 μM) within this extract synergized with phenformin at 100 μM.

Figure 13:
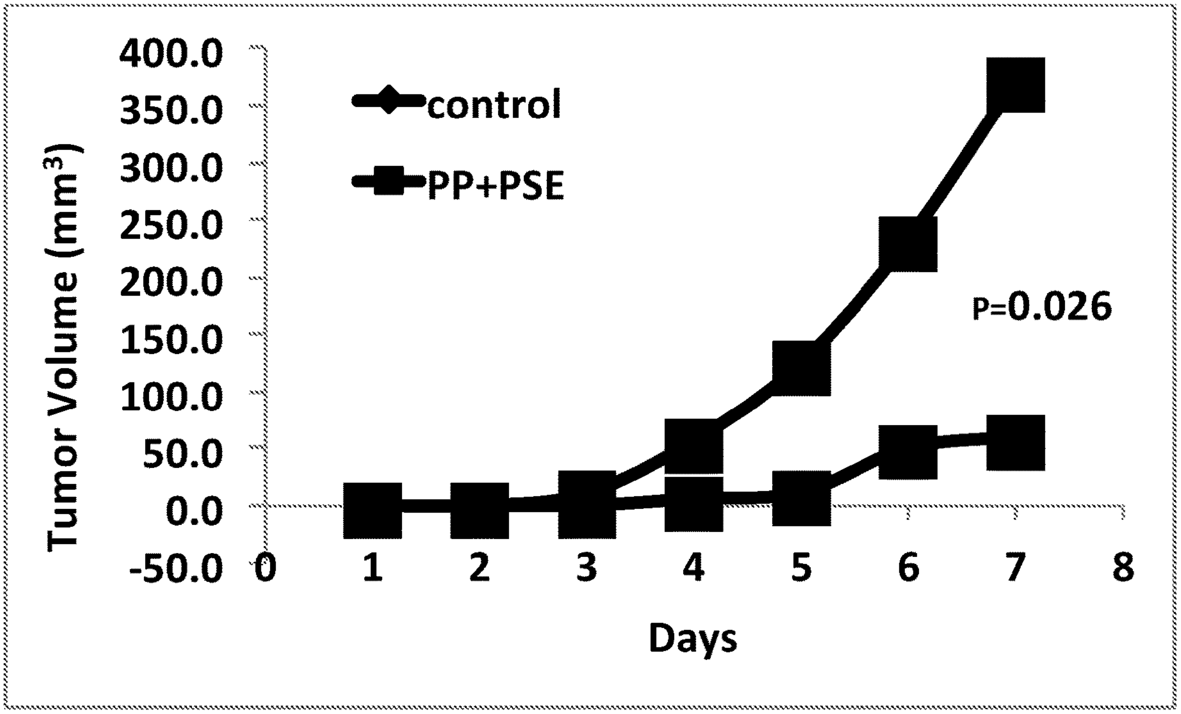
FIG. 13 shows Extracts containing GH and Paw Paw Paw acetogenins (mitochondrial complex I inhibitor) administered in combination inhibits B16-F10 melanoma tumor volume.
Figure 14:
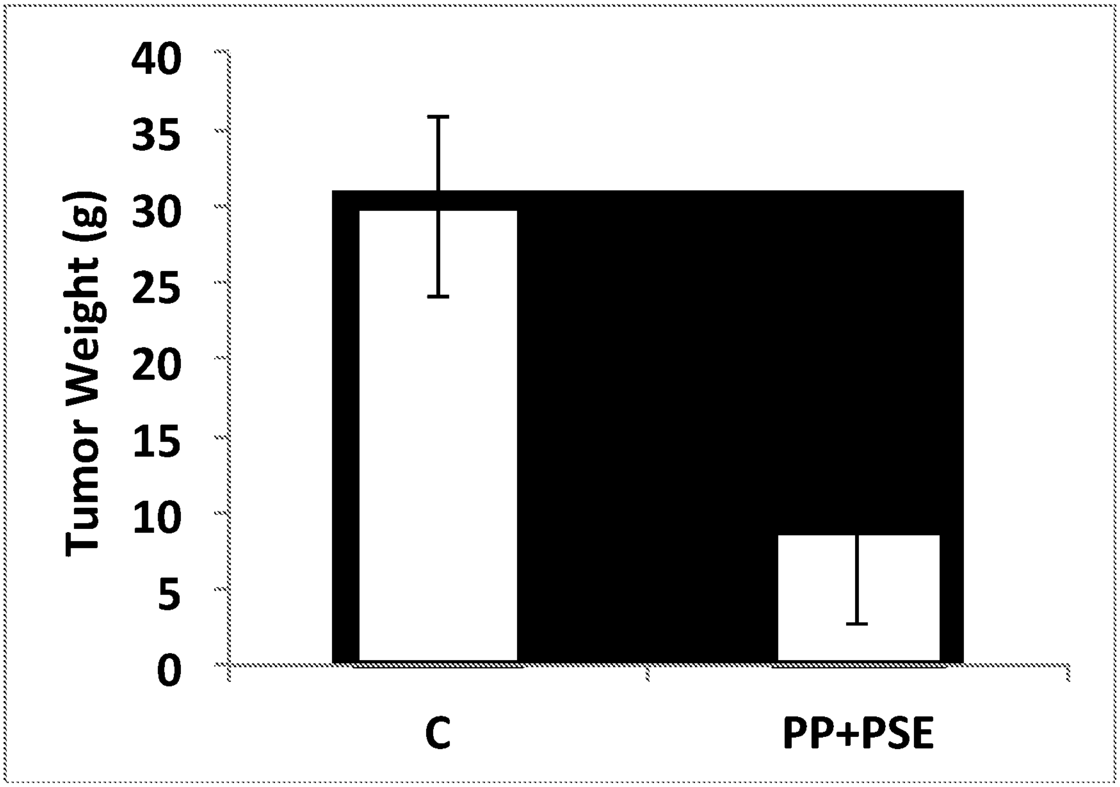
FIG. 14 shows Extracts containing GH and Paw Paw acetogenins (mitochondrial complex I inhibitor) administered in combination inhibits B16-F10 melanoma tumor weight.

Extracts containing GH and Paw Paw Paw acetogenins (mitochondrial complex I inhibitor) administered in combination inhibits B16-F10 melanoma tumor growth. The results presented in FIG. 13 and FIG. 14 demonstrate that the synergistic cytotoxicity observed with co treatment of GH or Peony seed extract (PSE) with Paw Paw extract (PP) in vitro also relates to substantially reduced B16-F10 melanoma tumor growth when administered in combination in a syngeneic mouse tumor model (C57BL/6). Extracts were administered orally by gavage each day starting on day one when tumors were palpable. Data is the average volume of 4 tumors for control and 5 tumors for treated mice. Treated mice received 0.5 mg/Kg Paw Paw extract and 6.8 mg/Kg PSE (containing 1.36 mg/Kg GH) per day by gavage.

GH inhibits expression of TXNIP and ARRDC4 mRNAs. The results presented in FIG. 8 and FIG. 9 indicate that the action of GH on p53-deficient cells differs in some fashion from that of the other glycolysis/lactic acid production inhibitors tested, 2-DG and GC, in that GH results in synergistic cytotoxicity when combined with mitochondrial complex I inhibitors while 2-DG and GC only result in a combined additive cytotoxic action. This result encouraged us to perform a differential gene expression analysis (RNA-Seq) to determine if it could provide mechanistic clues for the unique action of GH. The T98G human glioblastoma cell line was treated with the following for 2 hours before harvesting for RNA extraction and analysis: Untreated (solvent control), GH (8 μM), 2-DG (25 mM), phenformin (Ph-100 GH+Ph, and 2-DG+Ph. Analysis of the data revealed that the mRNA expression levels of two particular genes varied widely between the conditions containing GH and 2-DG (Table 1). TXNIP and ARRDC4 mRNA levels were substantially reduced (indicated by a minus sign in front of the fold change) in cells treated with GH alone and in combination with Ph while conditions containing 2-DG did not result in any change (indicated by NC) or resulted in an increase (indicated by a plus sign in front of the fold change) in their mRNA levels. Since the transcription factors (MondoA/Mlx complex) regulating the expression of the TXNIP gene is thought to be controlled by intermediates in the upper portion of the glycolytic pathway (12), GH may be negatively impacting this portion of glycolysis. Reduction in the levels of these intermediates by GH would prevent activation of the MondoA/Mlx transcription complex and would result in suppression of TXNIP transcription and TXNIP mRNA levels. Both of these gene products (TXNIP and ARRDC4) are thought to suppress glucose transport by enhancing degradation of glucose transporters (12).

TABLE 1

GH treatment rapidly reduces mRNAs encoding TXNIP and ARRDC4.

| | GH | GH + Ph | 2-DG | 2-DG + Ph | Ph |
|---|---|---|---|---|---|
| TXNIP | −88 | −34 | NC | +2 | −2.5 |
| ARRDC4 | −6 | −6 | +3 | NC | NC |

Figure 15:
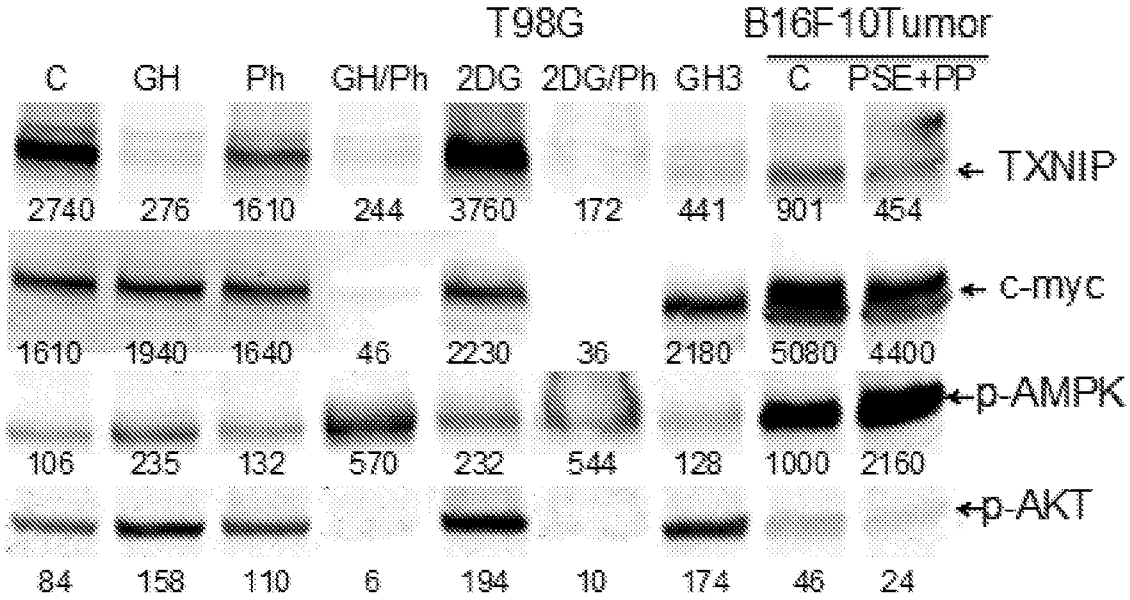
FIG. 15 shows GH, but not other glycolysis inhibitors, reduces TXNIP protein levels in T98G cell lines.
Figure 16:
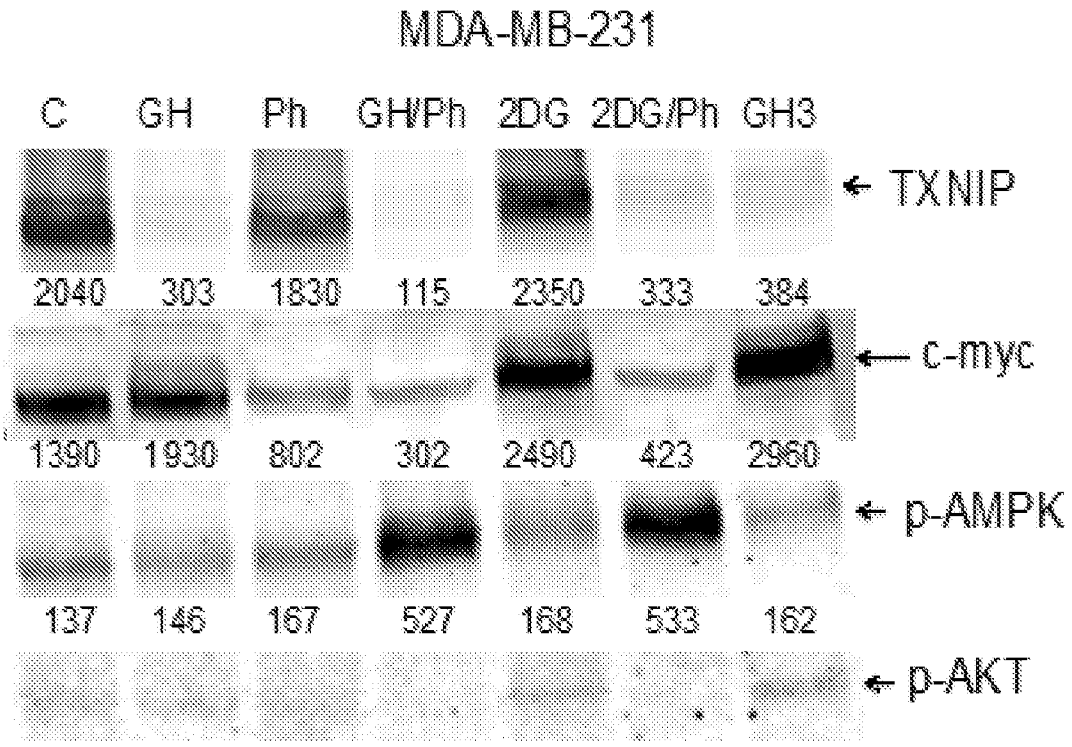
FIG. 16 shows GH, but not other glycolysis inhibitors, reduces TXNIP protein levels in MDA-MB-231 cell lines.
Figure 17:
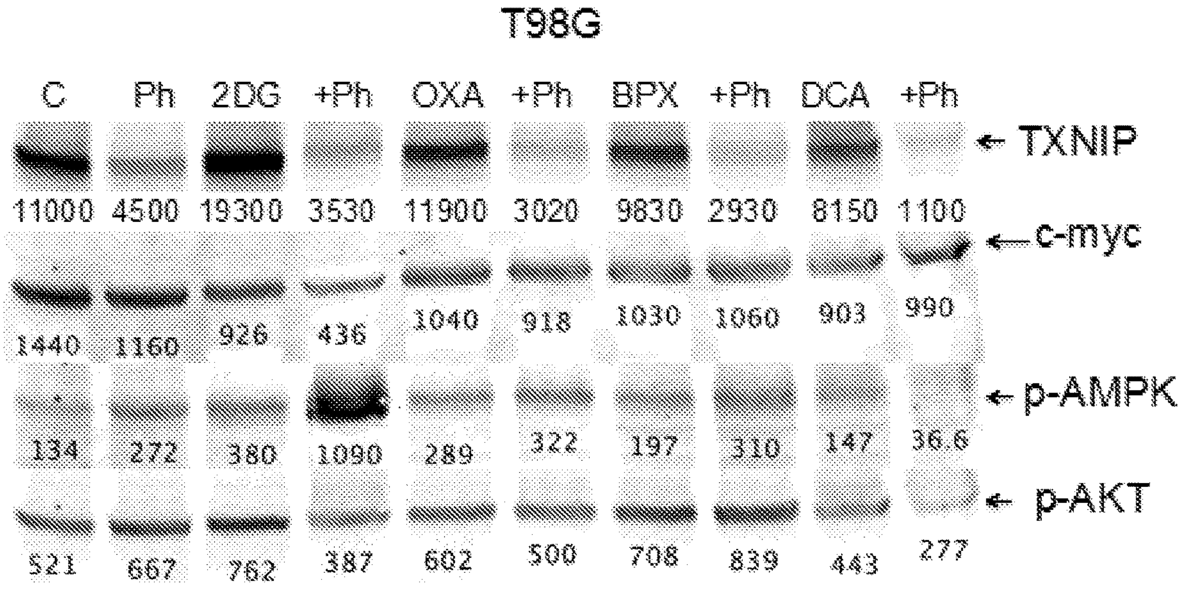
FIG. 17 shows other glycolysis inhibitors (all at 25 mM), oxamate (OXA, 25 mM), 3-bromopyruvate (BPX, 25 μM), dichloroacetate (DCA, 25 mM), tested alone do not substantially reduce TXNIP protein levels during a 6 hr treatment, while all of them in combination with Ph reduced TXNIP protein levels in T98G cell lines.
Figure 18:
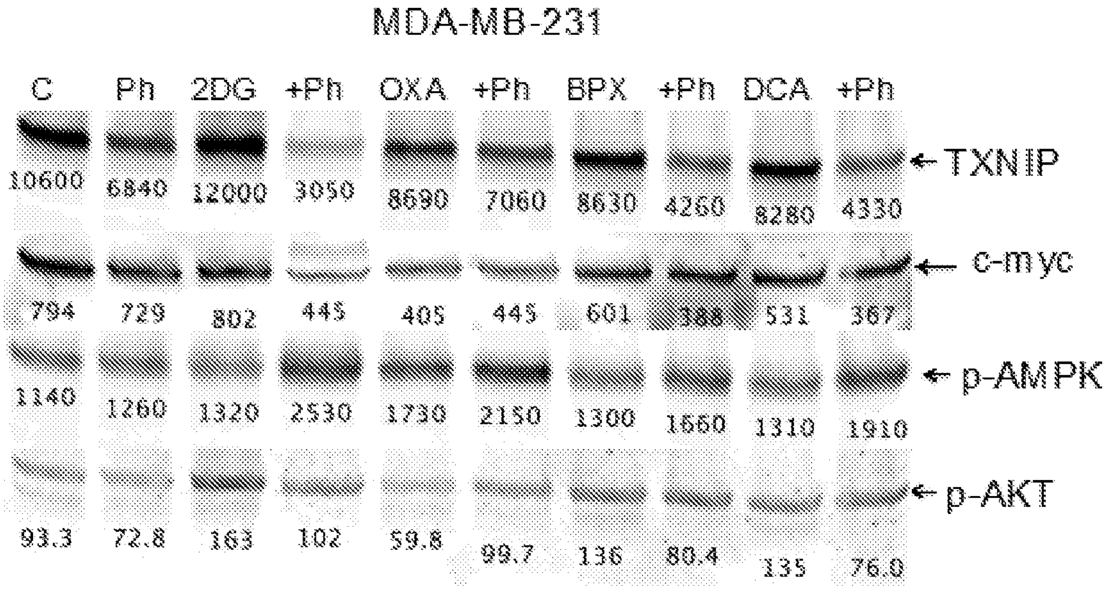
FIG. 18 shows other glycolysis inhibitors (all at 25 mM), oxamate (OXA, 25 mM), 3-bromopyruvate (BPX, 25 μM), dichloroacetate (DCA, 25 mM), tested alone do not substantially reduce TXNIP protein levels during a 6 hr treatment, while all of them in combination with Ph reduced TXNIP protein levels in MDA-MB-231 cell lines.

GH, but not other glycolysis inhibitors, reduces TXNIP protein levels. The results presented in the western blots of FIG. 15 and FIG. 16 indicate that treatment of the T98G and MDA-MB-231 cell lines with GH (8 μM) alone for 6 hrs (GH) or 3 hrs (GH3) resulted in dramatic reduction in the levels of TXNIP protein perhaps due to the reduction in TXNIP mRNA levels seen with GH alone in Table 1. In sharp contrast, treatment with the glycolysis inhibitor 2-DG (25 mM) alone increased TXNIP protein levels. GH or 2-DG in combination with Ph also results in reduction of TXNIP protein levels and this may be due to the activation (phosphorylation) of AMPK (p-AMPK). B16F10 tumors (FIG. 15) in mice treated with the extracts containing GH (PSE) and Paw Paw (PP) acetogenins (as performed in FIG. 13 and FIG. 14) also exhibited a reduction in TXNIP protein most likely caused by the activation of AMPK. AMPK activation has been previously shown to phosphorylate and cause the degradation of TXNIP during energy stress (13). The results in FIG. 17 and FIG. 18 indicate that the other glycolysis inhibitors (all at 25 mM), oxamate (OXA, 25 mM), 3-bromopyruvate (BPX, 25 μM), dichloroacetate (DCA, 25 mM), tested alone do not substantially reduce TXNIP protein levels during a 6 hr treatment, while all of them in combination with Ph reduced TXNIP protein levels.

Use of GH for treatment of type 2 diabetes and certain types of metabolic disorders. The reduction in expression of TXNIP mRNA and protein by GH may be therapeutically relevant for treatment of conditions accompanying some metabolic disorders and type-2 diabetes. Recently, research has demonstrated that TXNIP acts as a major regulator of glucose and lipid metabolism through actions on substrate utilization, hepatic glucose production, peripheral glucose uptake, regulation of pancreatic beta cell function and adipogenesis. In animal models, overexpression of TXNIP results in decreased energy expenditure, reduced insulin sensitivity in skeletal muscle and adipose tissue, and led to apoptosis of pancreatic beta cells (14). In contrast, animals deficient in TXNIP, or with downregulated TXNIP as might occur with GH treatment, were protected from diet-induced insulin resistance and type-2 diabetes (14).

Figure 19:
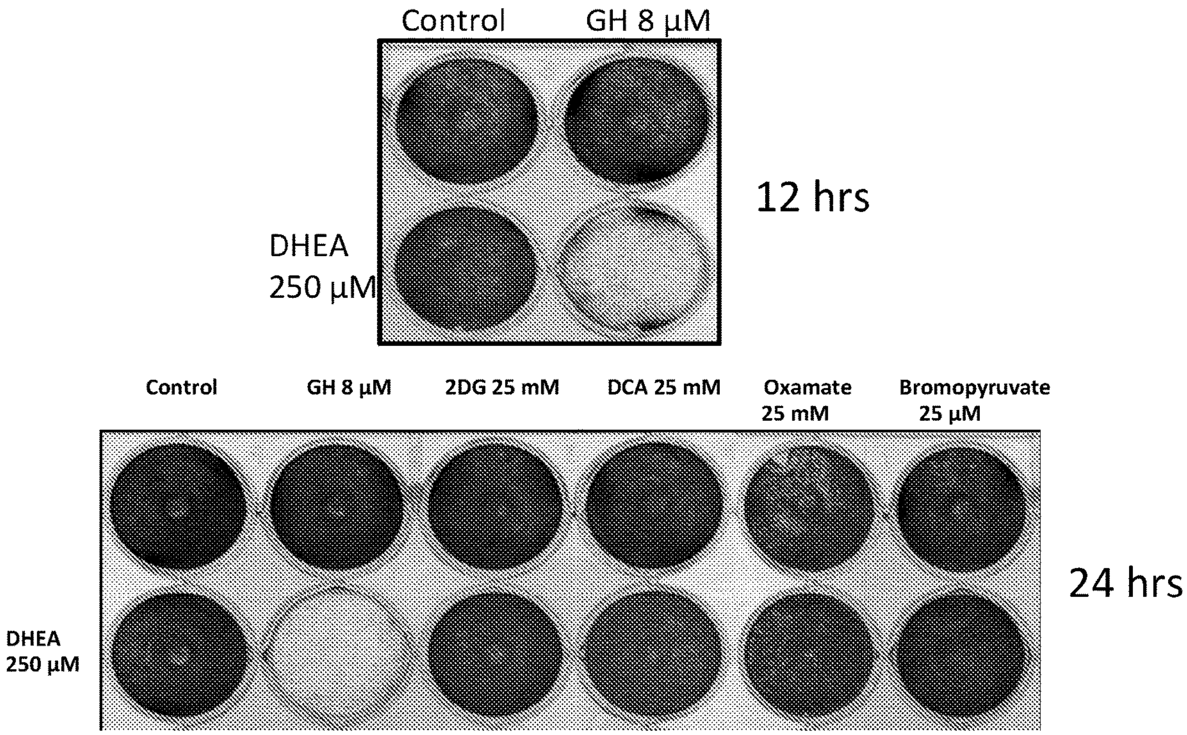
FIG. 19 shows a colony formation assay that indicates that GH (a glycolysis inhibitor) in combination with DHEA (a glucose-6-phosphate dehydrogenase inhibitor) is rapidly cytotoxic to T98G glioblastoma cells and in 12 h induces substantial cell death (greatly reduced cell staining).

GH, a glycolysis inhibitor, is cytotoxic to human tumor cells when used in combination with a Glucose-6-Phosphate Dehydrogenase inhibitor, dehydroepiandrosterone, (DHEA). To compensate for high ROS levels, cancer cells increase glycolysis and pentose phosphate cycle to provide reducing equivalents (NADH and NADPH) to neutralize hydro peroxides (15). The use of glycolysis inhibitors alone has not exhibited much success clinically for cancer therapy. It has been proposed (16) that combining pentose phosphate pathway inhibitors with glycolysis inhibitors may be a more effective anticancer therapeutic approach. FIG. 19 shows a colony formation assay that indicates that GH (a glycolysis inhibitor) in combination with DHEA (a glucose-6-phosphate dehydrogenase inhibitor) is rapidly cytotoxic to T98G glioblastoma cells and in 12 h induces substantial cell death (greatly reduced cell staining). The other glycolysis inhibitors tested in combination with DHEA were ineffective even at 24 h.

Figure 20:
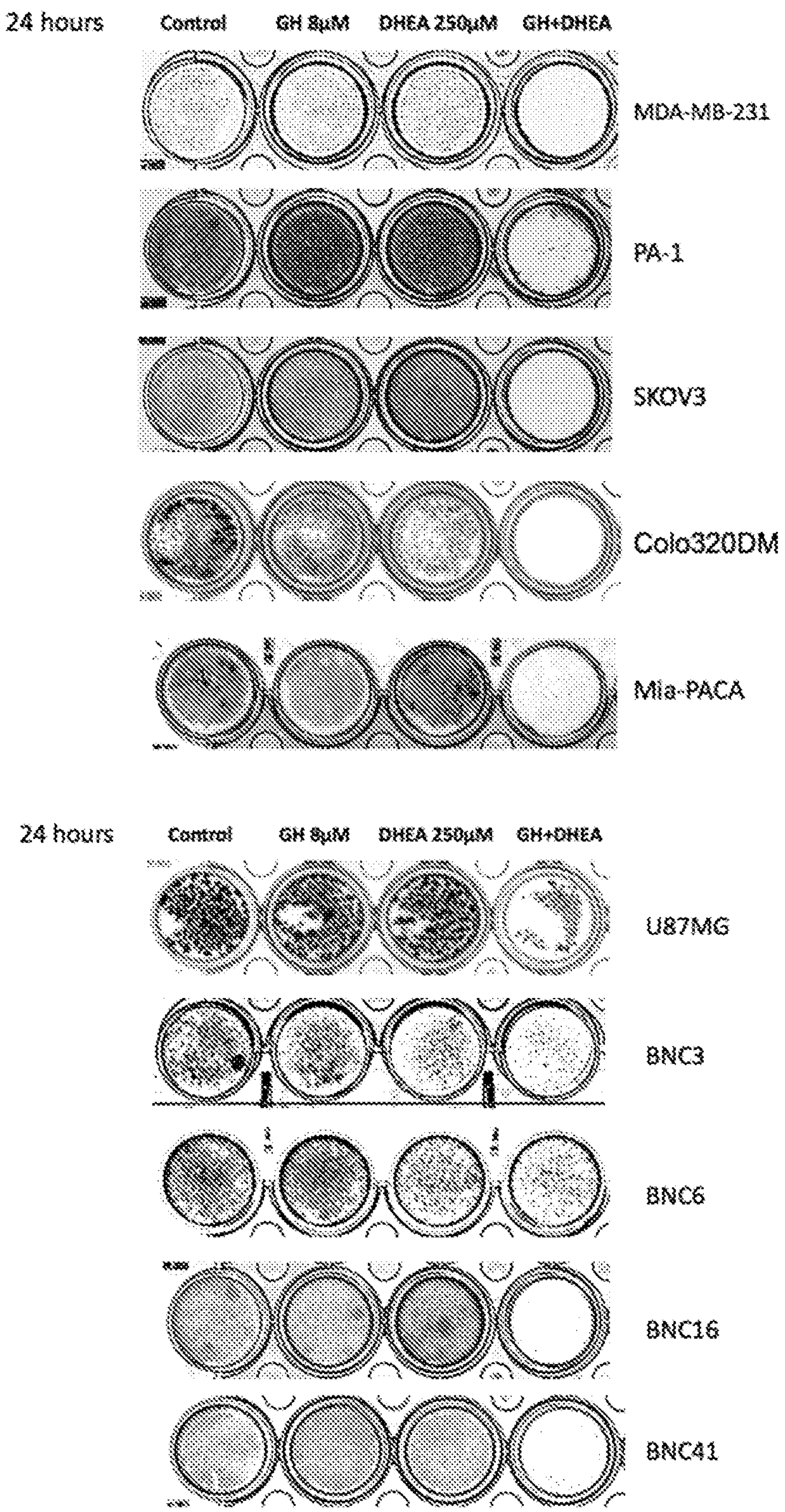
FIG. 20 shows a colony formation assay that indicates that GH (a glycolysis inhibitor) in combination with DHEA (a glucose-6-phosphate dehydrogenase inhibitor) is cytotoxic to MDA-MB-231 breast cancer cells, PA-1 Ovarian cancer, SKOV-3 ovarian cancer, Colo320DM colon cancer, Mia-PACA pancreatic cancer, U87MG Glioma cells, BNC3, BNC6, BNC16 and BNC41 patient derived Glioblastoma cells and in 24 h induces substantial cell death (greatly reduced cell staining).
Figure 21A:
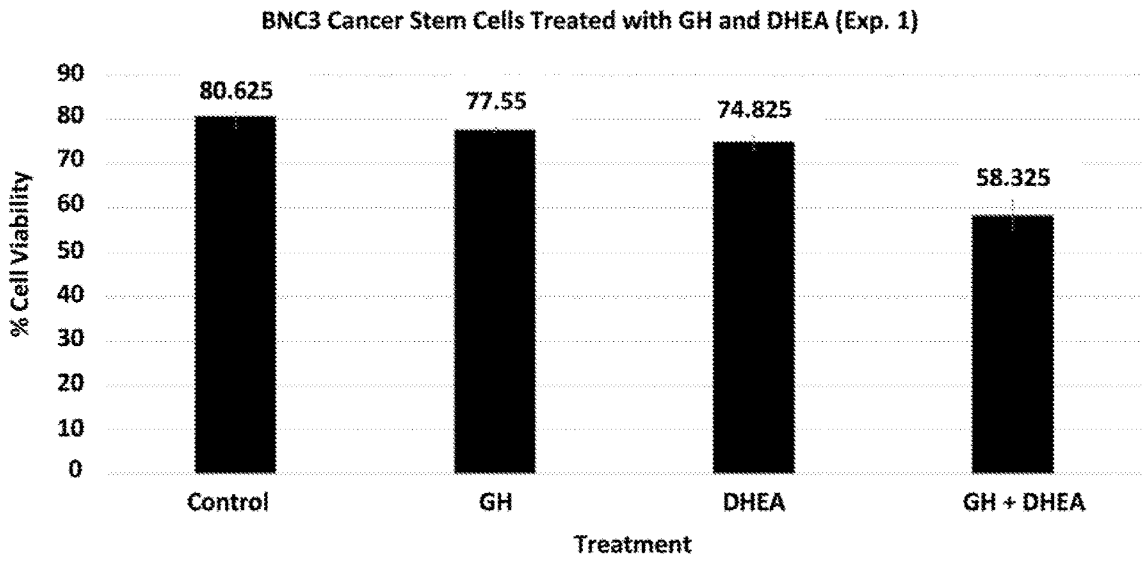
FIGS. 21 A-B. shows a graphic representation from two separate experiments of the percentage of cell viability as determined by Trypan Blue exclusion cell count that indicates that GH (a glycolysis inhibitor) in combination with DHEA (a glucose-6-phosphate dehydrogenase inhibitor) is cytotoxic to cancer stem cells (CSCs) grown from BNC3 patient derived Glioblastoma cells and in 24 h induces substantial cell death. A. first experiment, B. Second experiment.
Figure 21B:
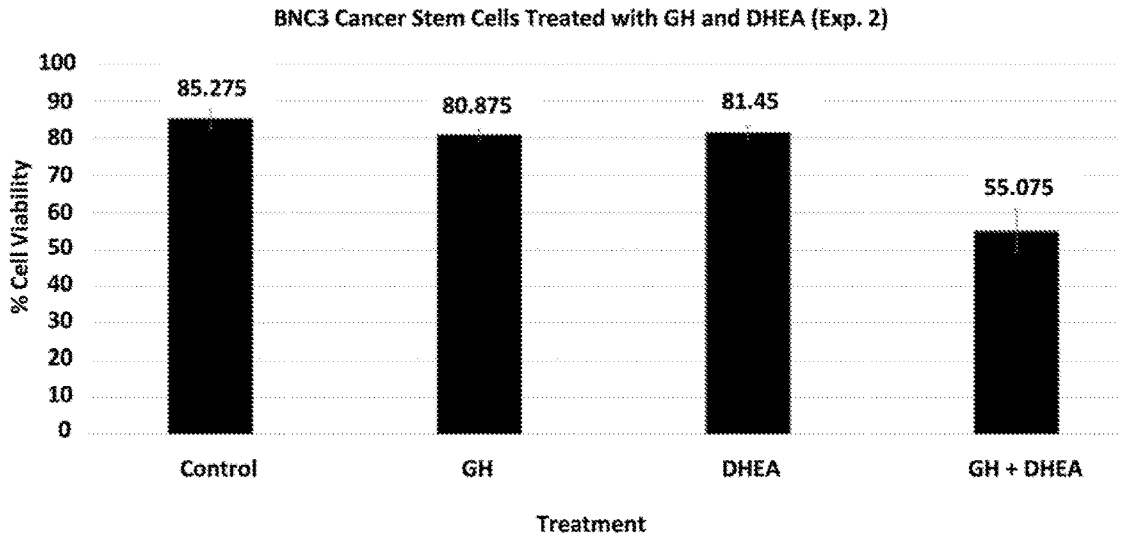

FIG. 20 shows a colony formation assay that indicates that GH (a glycolysis inhibitor) in combination with DHEA (a glucose-6-phosphate dehydrogenase inhibitor) is cytotoxic to MDA-MB-231 breast cancer cells, PA-1 Ovarian cancer, SKOV-3 ovarian cancer, Colo320DM colon cancer, Mia-PACA pancreatic cancer, U87MG Glioma cells, BNC3, BNC6, BNC16 and BNC41 patient derived Glioblastoma cells and in 24 h induces substantial cell death (greatly reduced cell staining).

FIGS. 21A-B and FIGS. 22A-B show a graphic representation from two separate experiments of the percentage of cell viability as determined by Trypan Blue exclusion cell count that indicates that GH (a glycolysis inhibitor) in combination with DHEA (a glucose-6-phosphate dehydrogenase inhibitor) is cytotoxic to cancer stem cells (CSCs) grown from BNC3 and BNC6 patient derived Glioblastoma cells and in 24 h induces substantial cell death.

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the term "subject" refers to a target of administration. The subject of the herein disclosed methods can be a mammal. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A "patient" refers to a subject afflicted with a disease or disorder. The term "patient" includes human and veterinary subjects.

As used herein, the term "effective amount" refers to an amount that is sufficient to achieve the desired result or to have an effect on an undesired condition. For example, the term "therapeutically effective amount" refers to an amount that is sufficient to achieve the desired therapeutic result or to have an effect on undesired symptoms, but is generally insufficient to cause adverse side effects. The specific therapeutically effective dose level for any particular subject will depend upon a variety of factors including the disorder being treated and the severity of the disorder; the specific composition employed; the age, body weight, general health, sex and diet of the subject; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

It will be understood that various details of the presently disclosed subject matter can be changed without departing from the scope of the subject matter disclosed herein. Furthermore, the foregoing description is for the purpose of illustration only, and not for the purpose of limitation.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Bost F, Decoux-Poullot A G, Tanti J F, Clavel S. Energy disruptors: rising stars in anticancer therapy? Oncogenesis 5:1-8, 2016.
2. Chaube B, Malvi P, Singh S V, Mohammad N, Meena A S, Bhat M K. Targeting metabolic flexibility by simultaneously inhibiting respiratory complex I and lactate generation retards melanoma progression. Oncotarget 6(35): 37281-37299, 2015.
3. Miskimins W K, Ahn H J, Kim J Y, Ryu S, Jung Y S, Choi J Y. Synergistic anti-cancer effect of phenformin and oxamate. PLoS One 9(1) e85576 (2014).
4. Cheong R I, Park E S, Liang J, Dennison J B, Tsavachidou D, Nguyen-Charles C, Wa Cheng K, Hall H, Zhang D, Lu Y, Ravoori M, Kundra V, Ajani J, Lee J S, Ki Hong W, Mills G B. Dual inhibition of tumor energy pathway by 2-deoxyglucose and metformin is effective against a broad spectrum of preclinical cancer models. Mol Cancer Ther 10(12):2350-2362, 2011.
5. Choi Y W, Lim I K. Sensitization of metformin-cytotoxicity by dichloroacetate via reprogramming glucose metabolism in cancer cells. Cancer Lett. 346(2):300-308, 2014.
6. Haugrud A B, Zhuang Y, Coppock J D, Miskimins W K. Dichloroacetate enhances apoptotic cell death via oxidative damage and attenuates lactate production in metformin-treated breast cancer cells. Breast Cancer Res Treat 147(3):539-550, 2014.
7. Ben Sahra I, Laurent K, Giuliano S, Larbret F, Ponzio G, Gounon P, Le Marchand-Brustel Y, Giorgetti-Peraldi S, Cormont M, Bertolotto C, Deckert M, Auberger P, Tanti J F, Bost F. Targeting cancer cell metabolism: the combination of metformin and 2-deoxyglucose induces p53-dependent apoptosis in prostate cancer cells. Cancer Res. 70(6):2465-2475, 2010.
8. Fato R, Bergamini C, Bortolus M, Maniero A L, Leoni S, Ohnishi T, Lenaz G. Differential effects of mitochondrial Complex I inhibitors on production of reactive oxygen species. Biochem Biophys Acta 1787(5):384-392, 2009.
9. Xue Y Q, Di J M, Luo Y, Cheng K J, Wei X, Shi Z. Resveratrol oligomers for the prevention and treatment of cancers. Oxid Med Cell Longev 2014:765832, 2014.
10. Marchiq I, Pouyssegur J. Hypoxia, cancer metabolism and the therapeutic benefit of targeting lactate/H(+) symporters. J Mol Med (Berl) 94(2):155-177, 2016.
11. Degli Esposti M, Ghelli A, Ratta M, Cortes D, Estornell E. Natural substances (acetogenins) from the family Annonaceae are powerful inhibitors of mitochondrial NADH dehydrogenase (Complex I). Biochem J 301:161-167, 1994.
12. O'Shea J M, Ayer D E. Coordination of nutrient availability and utilization by MAX- and MLX-centered transcription networks. Cold Spring Harb Perspect Med. 3(9):1-16, 2013.
13. Wu N, Zheng B, Shaywitz A, Dagon Y, Tower C, Bellinger G, Shen C H, Wen J, Asara J, McGraw T E, Kahn B B, Cantley L C. AMPK-dependent degradation of TXNIP upon energy stress leads to enhanced glucose uptake via GLUT1. Mol Cell. 49(6):1167-1175, 2013

14. Alhawiti N M, Al Mahri S, Aziz M A, Malik S S, Mohammad S. TXNIP in Metabolic Regulation: Physiological Role and Therapeutic Outlook. Curr Drug Targets.; 18(9):1095-1103, 2017.
15. Oberley L W, Buettner G R, Role of superoxide dismutase in cancer: a review, Cancer Research 39 (4), 1141-1149, 1979.
16. Li L, Fath M A, Scarbrough P M, Watson W H, Spitz D R. Combined inhibition of glycolysis, the pentose cycle, and thioredoxin metabolism selectively increases cytotoxicity and oxidative stress in human breast and prostate cancer. Redox Biol. 4:127-135, 2015.

What is claimed is:

1. A composition, comprising a gnetin H (GH) and a mitochondrial complex I inhibitor, wherein the mitochondrial complex I inhibitor is not metformin, and wherein the mitochondrial complex I inhibitor is selected from the group consisting of phenformin, rotenone, piericidinA, and acetogenins.

2. The composition of claim 1, wherein the GH is trans-GH.

3. The composition of claim 1, wherein the mitochondrial complex I inhibitor is acetogenins.

4. A method of treating cancer in a subject comprising administering to the subject a therapeutically effective amount of the composition of claim 1.

5. The method of claim 4, wherein the subject is a mammal.

6. The method of claim 5, wherein the mammal is a human.

7. The method of claim 4 wherein the subject lacks functional p53 or has dysfunctional p53.

8. The method of claim 4, wherein the administration is oral, transdermal, nasal, intracerebral, or by injection.

9. The method of claim 4, wherein the subject has functional p53.

10. A composition comprising a gnetin H (GH) and a glucose-6-phosphate dehydrogenase inhibitor, and wherein the glucose-6-phosphate dehydrogenase inhibitor is DHEA.

11. The composition of claim 10, wherein the GH is trans-GH.

12. A method of treating cancer in a subject comprising administering to the subject a therapeutically effective amount of the composition of claim 10.

13. The method of claim 12, wherein the subject is a mammal.

14. The method of claim 13, wherein the mammal is a human.

15. The method of claim 12, wherein the subject lacks functional p53 or has dysfunctional p53.

16. The method of claim 12, wherein the administration is oral, transdermal, nasal, intracerebral, or by injection.

* * * * *